(12) United States Patent
Iwasaki et al.

(10) Patent No.: US 10,689,349 B2
(45) Date of Patent: Jun. 23, 2020

(54) METHOD FOR PRODUCING INTERMEDIATE OF BIOTIN AND METHOD FOR PRODUCING BIOTIN

(71) Applicant: Tokuyama Corporation, Yamaguchi (JP)

(72) Inventors: Fumiaki Iwasaki, Yamaguchi (JP); Hiromasa Yamamoto, Yamaguchi (JP); Kenji Tanaka, Yamaguchi (JP); Masahiko Seki, Yamaguchi (JP); Yoshiki Seike, Yamaguchi (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 16/322,511

(22) PCT Filed: Jul. 26, 2017

(86) PCT No.: PCT/JP2017/027069
§ 371 (c)(1),
(2) Date: Feb. 1, 2019

(87) PCT Pub. No.: WO2018/025722
PCT Pub. Date: Feb. 8, 2018

(65) Prior Publication Data
US 2019/0382352 A1    Dec. 19, 2019

(30) Foreign Application Priority Data

Aug. 4, 2016 (JP) ................................. 2016-154072
Jan. 4, 2017 (JP) ................................. 2017-000106
Jan. 4, 2017 (JP) ................................. 2017-000128

(51) Int. Cl.
*C07D 233/34* (2006.01)
*C07D 487/04* (2006.01)
*C07D 491/048* (2006.01)
*C07D 495/04* (2006.01)

(52) U.S. Cl.
CPC ......... *C07D 233/34* (2013.01); *C07D 487/04* (2013.01); *C07D 491/048* (2013.01); *C07D 495/04* (2013.01)

(58) Field of Classification Search
CPC .......................... C07D 233/34; C07D 487/04
See application file for complete search history.

(56) References Cited

U.S. PATENT DOCUMENTS 3,876,656 A   4/1975   Aoki et al.
4,014,895 A   3/1977   Aoki et al.

FOREIGN PATENT DOCUMENTS

| JP | 49-20196 A | 2/1974 |
| JP | 49-117467 A | 11/1974 |
| JP | 49-127994 A | 12/1974 |

OTHER PUBLICATIONS

PCT International Search Report, dated Aug. 2018.
Shimizu et al., "Stereocontrol in the reduction of meso-imides using oxazaborolidine, leading to a facile synthesis of (+)-deoxybiotin", Tetrahedron Letters, vol. 40, 1999, 8873-76.
PCT International Preliminary Report on Patentability, dated Jan. 2019.

(Continued)

*Primary Examiner* — Shawquia Jackson
(74) *Attorney, Agent, or Firm* — Cahn & Samuels, LLP.

(57) ABSTRACT

In the method, a trione compound represented by the following formula (1) is (i) reduced by $NaAlH_2(OCH_2CH_2OCH_3)_2$ and subsequently further reduced by a metal borohydride salt, or (ii) reduced by calcium borohydride, thereby producing an amide alcohol compound represented by the following formula (3) (wherein, $R^1$ and $R^2$ may be the same or different and each represents a hydrogen atom or a protecting group of an ureylene group; $R^4$ represents an alkyl group, an aralkyl group, or an aryl group; and each of $R^5$, $R^6$, and $R^7$ represents a hydrogen atom, an alkyl group, an alkoxy group, or a halogen atom).

[Formula 1]

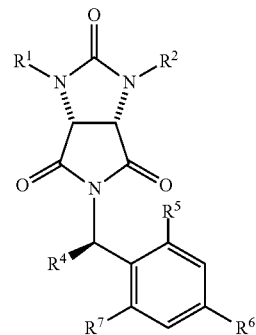

(1)

[Formula 3]

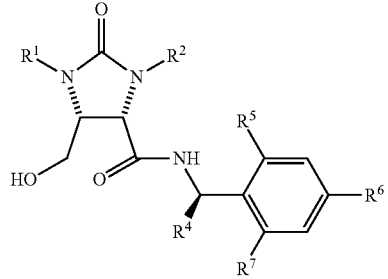

(3)

13 Claims, No Drawings

(56) References Cited

OTHER PUBLICATIONS

Fener, et al., "Study on the Asymmetric Total Synthesis of d-Biotin," Acta Pharmaceutica Sinica, 1999, 34(11), 822-827.
English Abstract of Fener, et al., "Study on the Asymmetric Total Synthesis of d-Biotin," Acta Pharmaceutica Sinica, 1999, 34(11), 822-827.

METHOD FOR PRODUCING INTERMEDIATE OF BIOTIN AND METHOD FOR PRODUCING BIOTIN

This application is a U.S. national stage application of PCT/JP2017/027069 filed on 26 Jul. 2017 and claims priority to Japanese patent document 2016-154072 filed on 4 Aug. 2016, Japanese patent document 2017-000106 filed on 4 Jan. 2017, and Japanese patent document 2017-000128 filed on 4 Jan. 2017, the entireties of which are incorporated herein by reference.

BACKGROUND OF THE INVENTION

The present invention relates to a novel method for producing an intermediate of biotin and a novel method for producing biotin in which the intermediate obtained by the method for producing an intermediate is used.

Biotin is a water-soluble vitamin used in medicines from which diabetes-preventing effect or the like is expected, and in feed additives or the like.

The biotin has a very long production process. Therefore, even the intermediate is produced through many processes. For example, even a thiolactone compound represented by the following formula (5)

[Formula 5]
Formula 5

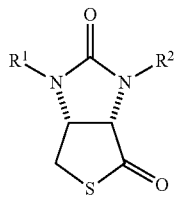

(5)

(wherein, $R^1$ and $R^2$ may be the same or different and each represents a hydrogen atom or a protecting group of an ureylene group), which is a representative intermediate of the biotin, is produced through very long processes as described below (see Patent Document 1). In the following processes, an example of an occasion when $R^1$ and $R^2$ are benzyl groups (Bn groups) (examples 1 and 3 of Patent Document 1) is shown.

[Formula 2]
Formula 2

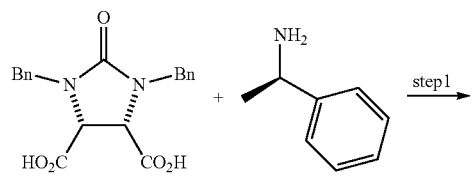

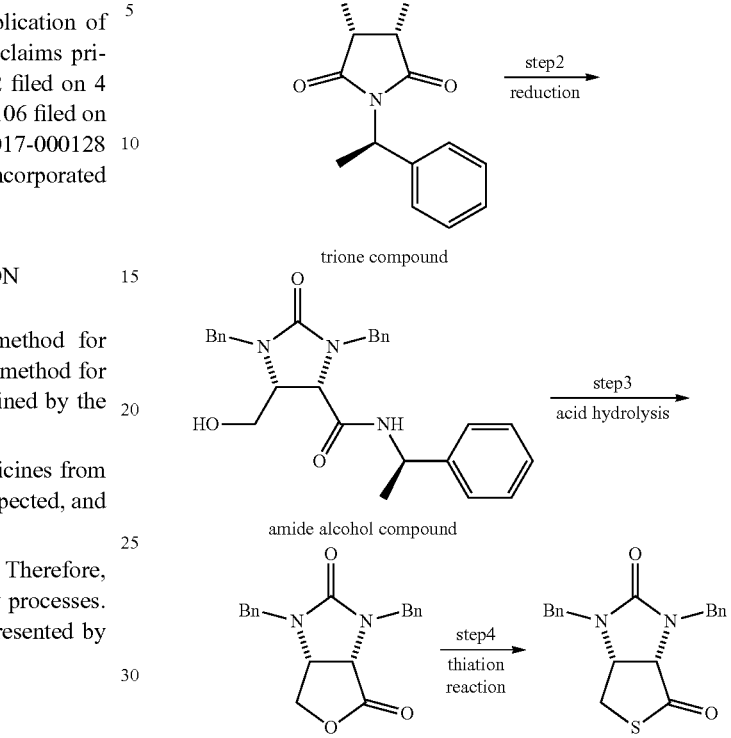

In the examples of Patent Document 1, a method is shown in which at first, an optically active amine such as α-phenethylamine ((R)-(+)-1-methylbenzylamine) is reacted with 1,3-dibenzyl-2-imidazolidone-cis-4,5-dicarboxylic acid to produce 1,3-dibenzyl-5-(α-phenethyl)-hexahydropyrrolo [3,4-a] imidazole-2,4,6-trione (step 1). Then, reduction (step 2), cyclization (step 3), and a thiation reaction (step 4) of 1,3-dibenzyl-5-(α-phenethyl)-hexahydropyrrolo [3,4-a] imidazole-2,4,6-trione are carried out to produce the thiolactone compound comprising a benzyl group. Besides, in Patent Document 1, it is shown that reactions of 7 processes are further carried out for the thiolactone compound, and the biotin which is a final product is obtained.

As described above, biotin is produced through a great many processes. Therefore, in order to lower the production cost of biotin, improvement of the production cost of the intermediate in each process, that is, improvement of the yield of each intermediate is also important.

However, it is known that, even in the processes above, in the reduction reaction (step 2), in addition to the amide alcohol compound which can eventually become biotin, an optical isomer of the amide alcohol compound is generated as an impurity, and the yield of the amide alcohol compound is decreased. The optical isomer impurity cannot become biotin, so that the yield decrease of the amide alcohol compound becomes a problem. As shown in example 3 of Patent Document 1, the amide alcohol compound, which is obtained by recrystallizing the product that is obtained in step 2 and comprises the impurity by a mixed solvent of water and isopropanol, is eventually obtained with a yield of about 50% only.

Patent Document 1: U.S. Pat. No. 3,876,656

BRIEF SUMMARY OF INVENTION

As described above, if the yield of the amide alcohol compound can be improved, the yield of biotin obtained eventually can also be improved.

Thus, the aim of the present invention is to provide a novel method for producing an intermediate of biotin, which is capable of improving the yield of the amide alcohol compound that is an intermediate of biotin. Besides, the aim of the present invention is to provide a novel method for producing biotin, which uses the intermediate as a raw material.

Inventors of the present invention made diligent studies to solve the problems above. Besides, the inventors of the present invention made various studies about production conditions capable of lowering the generation of the optical isomer impurity when the intermediate of biotin, specifically, the amide alcohol compound is produced. As a result, it is found that the problems above can be solved by using a preformed reduction agent, and the present invention is thus accomplished.

Furthermore, it is found that by also rethinking the method for producing an intermediate in addition to the amide alcohol compound, the yield of the biotin obtained eventually is improved and operation in all the production processes of the biotin can be improved, and the present invention is thus accomplished.

That is, the abstract of the present invention is as follows.

[1] A method in which an ureido compound represented by the following formula (11)

[Formula 11]
Formula 11

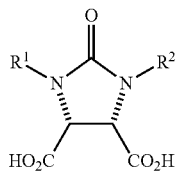

(11)

(wherein, $R^1$ and $R^2$ may be the same or different and represent a hydrogen atom or a protecting group of an ureylene group) is dehydrated by refluxing in a reaction solvent comprising an aromatic hydrocarbon based solvent which has a boiling point of 140° C. or more, thereby producing an anhydride compound represented by the following formula (7)

[Formula 7]
Formula 7

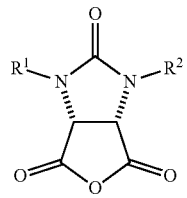

(7)

(wherein, $R^1$ and $R^2$ have the same meanings as those in the formula (11));

the anhydride compound and an optically active amine compound represented by the following formula (8)

[Formula 8]
Formula 8

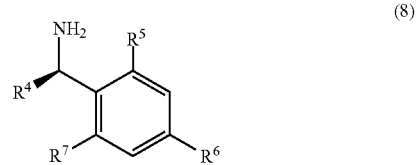

(8)

(wherein, $R^4$ represents an alkyl group, an aralkyl group, or an aryl group, and each of $R^5$, $R^6$, and $R^7$ represents a hydrogen atom, an alkyl group, an alkoxy group, or a halogen atom) are reacted in a reaction solvent comprising an aromatic hydrocarbon based solvent which has a boiling point of 140° C. or more, thereby producing a mixture which comprises an amide compound I represented by the following formula (9)

[Formula 9]
Formula 9

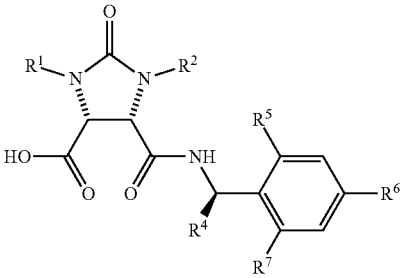

(9)

(wherein, $R^1$ and $R^2$ have the same meanings as those in the formula (11), and $R^4$, $R^5$, $R^6$, and $R^7$ have the same meanings as those in the formula (8)) and an amide compound II represented by the following formula (10)

[Formula 10]
Formula 10

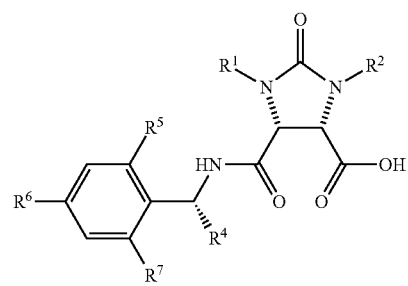

(10)

(wherein, $R^1$ and $R^2$ have the same meanings as those in the formula (11), and $R^4$, $R^5$, $R^6$, and $R^7$ have the same meanings as those in the formula (8));

a first reaction solution comprising the obtained mixture and the aromatic hydrocarbon based solvent which has a boiling point of 140° C. or more is refluxed to dehydrate the mixture, thereby producing a trione compound represented by the following formula (1)

[Formula 1]
Formula 1

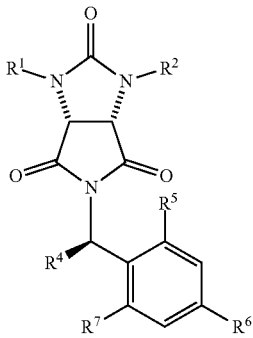
(1)

(wherein,

R¹ and R² have the same meanings as those in the formula (11), and R⁴, R⁵, R⁶, and R⁷ have the same meanings as those in the formula (8));

the trione compound is (i) reduced by $NaAlH_2(OCH_2CH_2OCH_3)_2$ and subsequently further reduced by a metal borohydride salt, or (ii) reduced by calcium borohydride, thereby producing an amide alcohol compound represented by the following formula (3)

[Formula 3]
Formula 3

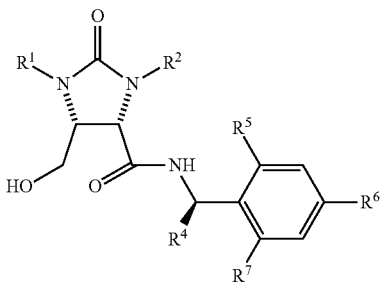
(3)

(wherein,

R¹ and R² have the same meanings as those in the formula (11), and R⁴, R⁵, R⁶, and R⁷ have the same meanings as those in the formula (8)); and the amide alcohol compound is cyclized in the presence of hydrogen chloride in a solvent comprising an alkylene glycol monoalkyl ether in which the total number of carbon atoms in a molecule is 2 to 12, thereby producing a lactone compound represented by the following formula (4)

[Formula 4]
Formula 4

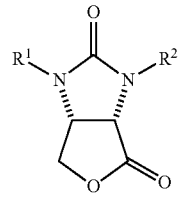
(4)

(wherein,

R¹ and R² have the same meanings as those in the formula (11)).

[2] A method in which a trione compound represented by the following formula (1)

[Formula 1]
Formula 1

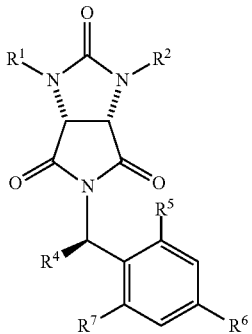
(1)

(wherein,

R¹ and R² may be the same or different and each represents a hydrogen atom or a protecting group of an ureylene group;

R⁴ represents an alkyl group, an aralkyl group, or an aryl group; and each of R⁵, R⁶, and R⁷ represents a hydrogen atom, an alkyl group, an alkoxy group, or a halogen atom) is (i) reduced by $NaAlH_2(OCH_2CH_2OCH_3)_2$ and subsequently further reduced by a metal borohydride salt, or (ii) reduced by calcium borohydride, thereby producing an amide alcohol compound represented by the following formula (3)

[Formula 3]
Formula 3

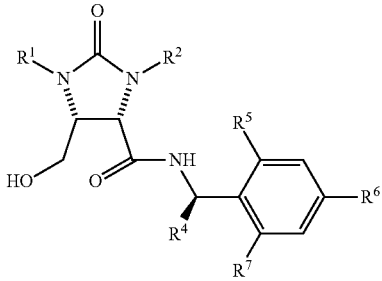
(3)

(wherein,

R¹, R², R⁴, R⁵, R⁶, and R⁷ have the same meanings as those in the formula (1)).

[3] A method in which the amide alcohol compound represented by the formula (3) is produced by the method according to [2], and subsequently the amide alcohol compound is cyclized in the presence of hydrogen chloride in a solvent comprising an alkylene glycol monoalkyl ether in which the total number of carbon atoms in a molecule is 2 to 12, thereby
producing a lactone compound represented by the following formula (4)

[Formula 4]
Formula 4

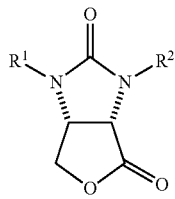

(4)

(wherein,
$R^1$ and $R^2$ have the same meanings as those in the formula (1)).

[4] A method in which the lactone compound represented by the formula (4) is produced by the method according to [3], and subsequently the lactone compound is reacted with a thiation agent, thereby
producing a thiolactone compound represented by the following formula (5)

[Formula 5]
Formula 5

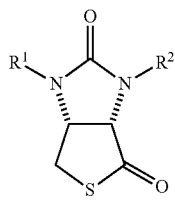

(5)

(wherein,
$R^1$ and $R^2$ have the same meanings as those in the formula (1)).

[5] A method in which after producing the thiolactone compound represented by the formula (5) by the method according to [4], the thiolactone compound is used as a raw material to produce biotin represented by the following formula (6).

[Formula 6]
Formula 6

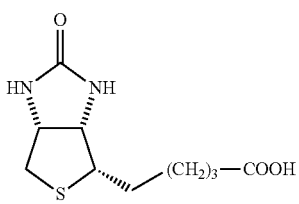

(6)

[6] The method according to [2], wherein
an anhydride compound represented by the following formula (7)

[Formula 7]
Formula 7

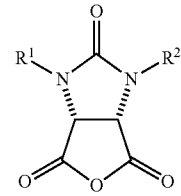

(7)

(wherein,
$R^1$ and $R^2$ have the same meanings as those in the formula (1)) and an optically active amine compound represented by the following formula (8)

[Formula 8]
Formula 8

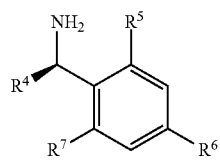

(8)

(wherein,
$R^4$, $R^5$, $R^6$, and $R^7$ have the same meanings as those in the formula (1))
are reacted in a reaction solvent comprising an aromatic hydrocarbon based solvent which has a boiling point of 140° C. or more, thereby
producing a mixture which comprises an amide compound I represented by the following formula (9)

[Formula 9]
Formula 9

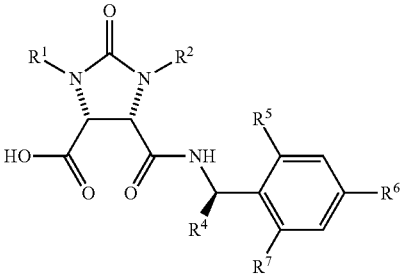

(9)

(wherein,
$R^1$, $R^2$, $R^4$, $R^5$, $R^6$, and $R^7$ have the same meanings as those in the formula (1)) and
an amide compound II represented by the following formula (10)

[Formula 10]
Formula 10

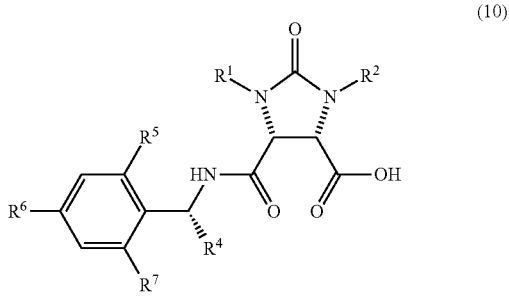

(wherein, $R^1$, $R^2$, $R^4$, $R^5$, $R^6$, and $R^7$ have the same meanings as those in the formula (1));

the first reaction solution comprising the obtained mixture and the aromatic hydrocarbon based solvent which has a boiling point of 140° C. or more is refluxed to dehydrate the mixture, thereby producing the trione compound represented by the formula (1); and subsequently the obtained trione compound is (i) reduced by $NaAlH_2(OCH_2CH_2OCH_3)_2$, and subsequently further reduced by the metal borohydride salt, or (ii) reduced by a polyvalent metal salt of the calcium borohydride, thereby producing the amide alcohol compound represented by the formula (3).

[7] The method according to [6], wherein an ureido compound represented by the following formula (11)

[Formula 11]
Formula 11

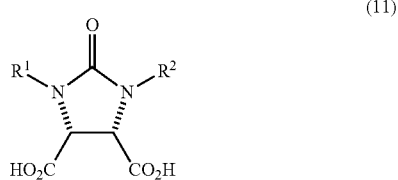

(wherein, $R^1$ and $R^2$ have the same meanings as those in the formula (1)) is dehydrated by refluxing in a reaction solvent comprising an aromatic hydrocarbon based solvent which has a boiling point of 140° C. or more, thereby producing the anhydride compound represented by the formula (7), and subsequently the obtained anhydride compound is reacted with the optically active amine compound represented by the formula (8).

[8] The method according to any one of [1] to [7], wherein a reaction temperature at the time of reducing by the calcium borohydride in (ii) is −30° C. or more and 50° C. or less.

[9] The method according to any one of [1] to [7], wherein the reaction temperature at the time of reducing by $NaAlH_2(OCH_2CH_2OCH_3)_2$ in (i) is −20° C. or more and 5° C. or less.

[10] The method according to any one of [1] to [7], wherein the reduction of the trione compound represented by the formula (1) is implemented in an alcohol which has a carbon number of 1 to 6.

[11] The method according to any one of [1], and [3] to [5], wherein the total number of carbon atoms in a molecule of the alkylene glycol monoalkyl ether is 2 to 6.

[12] The method according to any one of [1], [6], and [7], wherein a second reaction solution which comprises the anhydride compound represented by the formula (7) and a reaction solvent comprising an aromatic hydrocarbon based solvent which has a boiling point of 140° C. or more is produced, and subsequently the second reaction solution and the optically active amine compound represented by the formula (8) are mixed, thereby producing the mixture which comprises the amide compound I represented by the formula (9) and the amide compound II represented by the formula (10).

Effects

According to the method of the present invention, the yield of the amide alcohol compound which is the intermediate of the biotin can be improved. Besides, when the amide alcohol compound is produced, the generation of the impurity of the optical isomer can be lowered, so that it is also easy to increase the purity of the amide alcohol compound. As a result, according to the method of the present invention, the biotin can be produced efficiently.

Particularly, the lactone compound which is a raw material of the biotin can be produced with few by-products and a good yield by cyclizing the amide alcohol compound in the presence of hydrogen chloride in the solvent comprising an alkylene glycol monoalkyl ether in which the total number of carbon atoms in the molecule is 2 to 12. As a result, the biotin can be produced more efficiently.

In addition, by producing the trione compound which is also an intermediate of the biotin in a reaction solvent comprising an aromatic hydrocarbon based solvent which has a boiling point of 140° C. or more, the trione compound can be produced with a good operation, and thus the biotin obtained eventually can be produced efficiently by using the method.

DETAILED DESCRIPTION OF INVENTION

A lactone producing method of an embodiment of the present invention is characterized in that:

an ureido compound represented by the following formula (11)

[Formula 11]
Formula 11

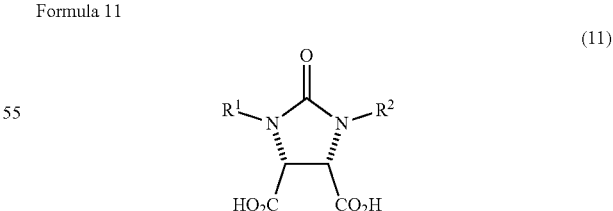

(wherein, $R^1$ and $R^2$ may be the same or different and represent a hydrogen atom or a protecting group of an ureylene group) is dehydrated by refluxing in a reaction solvent comprising an aromatic hydrocarbon based solvent which has a boiling point of 140° C. or more, thereby producing an anhydride compound represented by the following formula (7)

[Formula 7]
Formula 7

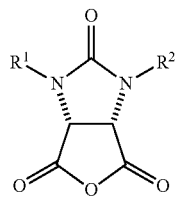
(7)

(wherein,

R¹ and R² have the same meanings as those in the formula (11));

the anhydride compound and an optically active amine compound represented by the following formula (8)

[Formula 8]
Formula 8

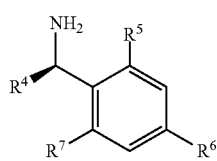
(8)

(wherein, $R^4$ represents an alkyl group, an aralkyl group, or an aryl group, and each of $R^5$, $R^6$, and $R^7$ represents a hydrogen atom, an alkyl group, an alkoxy group, or a halogen atom) are reacted in a reaction solvent comprising an aromatic hydrocarbon based solvent which has a boiling point of 140° C. or more, thereby producing a mixture which comprises an amide compound I represented by the following formula (9)

[Formula 9]
Formula 9

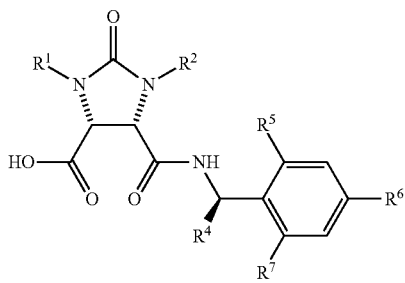
(9)

(wherein, $R^1$ and $R^2$ have the same meanings as those in the formula (11), and $R^4$, $R^5$, $R^6$, and $R^7$ have the same meanings as those in the formula (8)) and an amide compound II represented by the following formula (10)

[Formula 10]
Formula 10

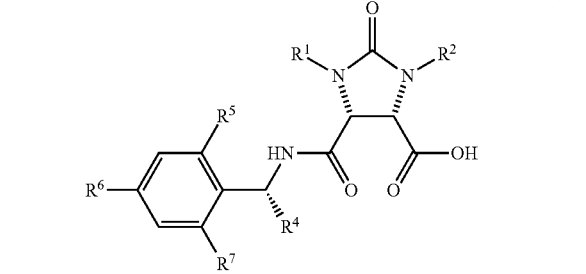
(10)

(wherein, $R^1$ and $R^2$ have the same meanings as those in the formula (11), and $R^4$, $R^5$, $R^6$, and $R^7$ have the same meanings as those in the formula (8));

a first reaction solution comprising the obtained mixture and the aromatic hydrocarbon based solvent which has a boiling point of 140° C. or more is refluxed to dehydrate the mixture, thereby producing a trione compound represented by the following formula (1)

[Formula 1]
Formula 1

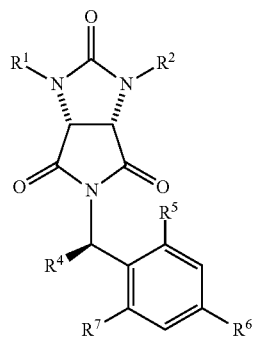
(1)

(wherein, $R^1$ and $R^2$ have the same meanings as those in the formula (11), and $R^4$, $R^5$, $R^6$, and $R^7$ have the same meanings as those in the formula (8));

the trione compound is (i) reduced by $NaAlH_2(OCH_2CH_2OCH_3)_2$ and subsequently further reduced by a metal borohydride salt, or (ii) reduced by calcium borohydride, thereby producing an amide alcohol compound represented by the following formula (3)

[Formula 3]
Formula 3

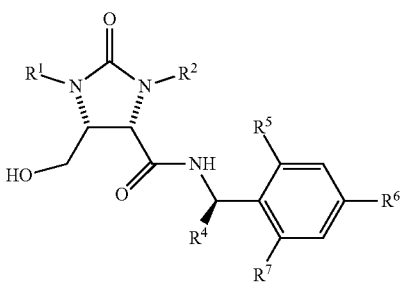
(3)

(wherein,

R¹ and R² have the same meanings as those in the formula (11), and R⁴, R⁵, R⁶, and R⁷ have the same meanings as those in the formula (8)); and the amide alcohol compound is cyclized in the presence of hydrogen chloride in a solvent comprising an alkylene glycol monoalkyl ether in which the total number of carbon atoms in a molecule is 2 to 12, thereby producing a lactone compound represented by the following formula (4)

[Formula 4]
Formula 4

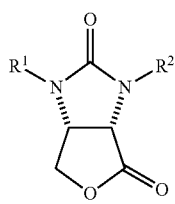
(4)

(wherein,

R¹ and R² have the same meanings as those in the formula (11)).

In the following, the producing method of the intermediate of biotin and the producing method of biotin of the embodiment of the present invention are described specifically.

At first, the producing method of the trione compound which is the intermediate of biotin is described.

The trione compound can be synthesized by a known method, for example, the method mentioned in Patent Document 1. However, because of a low solubility in an organic solvent, the compound which is a raw material immediately before the trione compound is preferably produced by the following method.

(Preferred Producing Method of Trione Compound)

The trione compound used in the embodiment of the present invention is preferably produced by the following method. At first, the ureido compound is dehydrated to produce the anhydride compound, and the anhydride compound is reacted with the optically active amine compound to produce the mixture comprising the amide compound I and the amide compound II. Then, the trione compound is produced by dehydrating the mixture. At first, the producing method of the anhydride compound is described.

(Producing Method of Anhydride Compound)

The anhydride compound is not particularly limited and is preferably produced by the following method. That is, the anhydride compound is preferably produced by dehydrating the ureido compound represented by the following formula (11).

[Formula 11]
Formula 11

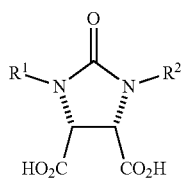
(11)

The ureido compound is a known compound, and is the compound illustrated in Patent Document 1.

In the formula (11), R¹ and R² may be the same or different and each represents a hydrogen atom or a protecting group of an ureylene group. The protecting group of the ureylene group may be an alkyl group, an aryl group, an aralkyl group, or an acyl group. Above all, an alkyl group with a carbon number of 1 to 10, an aryl group with a carbon number of 5 to 10, an aralkyl group with a carbon number of 6 to 11, or an acyl group with a carbon number of 1 to 11 is preferable. Particularly, each of R¹ and R² is preferably a benzyl group.

Here, the ureylene group is a group represented by —NHCONH—. The protecting group of the ureylene group is a group that is substituted to a ureido group and is inactivated in a predetermined reaction. After the predetermined reaction, the ureylene group is formed by deprotection.

The anhydride compound can be produced by dehydrating and cyclizing the ureido compound represented by the formula (11). The dehydration of the ureido compound is preferably implemented in an aromatic hydrocarbon based solvent which has a boiling point of 140° C. or more. The ureido compound can be easily dehydrated by using the aromatic hydrocarbon based solvent.

In order to dehydrate the ureido compound in the aromatic hydrocarbon based solvent, the following method is preferably adopted. That is, a solution in which the ureido compound is dissolved in the aromatic hydrocarbon based solvent is prepared. Then, water generated in the reaction mixture may be taken out of the mixture while maintaining the solution at a reflux temperature.

Conditions in a case that the ureido compound is dehydrated are not particularly limited, and the following conditions are preferably adopted.

Specifically, considering post-processes and the ease of dehydration or the like, preferably 1 to 20 mL, more preferably 2 to 6 mL of the aromatic hydrocarbon based solvent is used for 1 g of the ureido compound.

In addition, when the dehydration reaction is carried out, a state that the reaction mixture is sufficiently mixed is preferable and stirring and mixing is preferable. The temperature (reaction temperature) at the time of dehydration is preferably set to the reflux temperature of the reaction solution, specifically, preferably in a range of 140° C. to 210° C., and more preferably in a range of 160 to 190° C. The dehydration reaction may be implemented in any condition of reduced pressure, ordinary pressure or increased pressure. However, in order to carry out the dehydration sufficiently, the dehydration is preferably implemented in a range from reduced pressure to ordinary pressure. Above all, when the aromatic hydrocarbon based solvent is used, the aromatic hydrocarbon based solvent easily forms an azeotropic mixture with water and the dehydration reaction proceeds easily, so that the dehydration reaction may be implemented under ordinary pressure.

A reaction time is not particularly limited either and may be appropriately determined by confirming the generation state of the anhydride compound. That is, an amount of the azeotropic water is confirmed to confirm the progress of the reaction, and the reaction may be implemented until the azeotropic water does not exist. Usually, 0.5 to 20 hours is sufficient. In addition, a reaction atmosphere is not particularly limited either, and the reaction can be implemented under an air atmosphere or an inert gas atmosphere such as nitrogen gas or the like.

The dehydration reaction above can be implemented by known equipment. For example, a device provided with a cooling condenser (for example, Dean-Stark dehydration device) can be used to implement the dehydration reaction.

The aromatic hydrocarbon based solvent is not particularly limited as long as the boiling point is 140° C. or more. Considering the industrial production, ease of removal and usefulness or the like of the solvent itself, the boiling point of the aromatic hydrocarbon based solvent is preferably 140 to 210° C., and more preferably 160 to 190° C.

The aromatic hydrocarbon based solvent can use commercially available aromatic hydrocarbon based solvents without any limitation. Specifically, the aromatic hydrocarbon based solvent is preferably a solvent which has a boiling point of 140° C. or more and in which 1 to 6 hydrogen atoms are substituted by alkyl groups with a carbon number of 1 to 3 in benzene or in which 2 to 6 hydrogen atoms are substituted by halogen atoms in benzene. When a specific solvent is illustrated, mesitylene (the boiling point is 165° C.), pseudocumene (the boiling point is 169° C.), hemimellitene (the boiling point is 176° C.), cumene (the boiling point is 152° C.), 1,2-dichlorobenzene (the boiling point is 180° C.), 1,3-dichlorobenzene (the boiling point is 172° C.), 1,4-dichlorobenzene (the boiling point is 174° C.) are listed. These solvents may be used alone, or a mixed solvent of plural kinds of solvents may be used. Above all, considering the ease of the dehydration, the solubility of the anhydride compound, and the ease of operation in the following reaction or the like, mesitylene (the boiling point is 165° C.) is particularly preferable.

In the embodiment of the present invention, when the aromatic hydrocarbon based solvent which has a boiling point of 140° C. or more is used in the dehydration reaction of the ureido compound, after the dehydration reaction is ended, a second reaction solution that comprises the anhydride compound represented by the following formula (7) and the reaction solvent which comprises the aromatic hydrocarbon based solvent with a boiling point of 140° C. or more is obtained. In the embodiment of the present invention, the anhydride compound can be temporarily taken out from the reaction mixture, but in order to further improve the operation, the second reaction solution is preferably used directly in the reaction (the reaction with the optically active amine compound) of the next process.

[Formula 7]
Formula 7

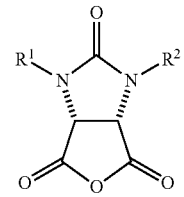

(7)

(wherein,
$R^1$ and $R^2$ have the same meanings as those in the formula (11)).

(Reaction Conditions with Optically Active Amine Compound)

In the embodiment of the present invention, the anhydride compound represented by the formula (7) is reacted with the optically active amine compound represented by the following formula (8)

[Formula 8]
Formula 8

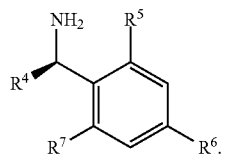

(8)

Here, $R^4$ represents an alkyl group, an aralkyl group, and an aryl group. Above all, an alkyl group with a carbon number of 1 to 10, an aralkyl group with a carbon number of 6 to 11, or an aryl group with a carbon number of 5 to 10 is preferable. Particularly, $R^4$ is preferably a methyl group.

In addition, each of $R^5$, $R^6$, and $R^7$ represents a hydrogen atom, an alkyl group, an alkoxy group, or a halogen atom. Above all, $R^5$, $R^6$, and $R^7$ are preferably a hydrogen atom, an alkyl group with a carbon number of 1 to 10, an alkoxy group with a carbon number of 1 to 10, or a halogen atom. Particularly, each of $R^5$, $R^6$, and $R^7$ is preferably a hydrogen atom.

The anhydride compound represented by the formula (7) and the optically active amine compound represented by the formula (8) are preferably reacted in a reaction solvent which comprises an aromatic hydrocarbon based solvent with a boiling point of 140° C. or more. The aromatic hydrocarbon based solvent may be the same solvent as the aromatic hydrocarbon based solvent in "producing method of anhydride compound", and the preferable solvents are the same preferable solvents for the same reason.

Here, the anhydride compound can also be temporarily taken out from the reaction mixture and reacted with the optically active amine compound separately in a reaction solvent comprising an aromatic hydrocarbon based solvent which has a boiling point of 140° C. or more. However, in order to further improve the operation, the reaction is preferably promoted by mixing the second reaction solution, which comprises the anhydride compound and the reaction solvent that comprises the aromatic hydrocarbon based solvent with a boiling point of 140° C. or more, and the optically active amine compound. Furthermore, the reaction solvent may comprise water or the like which is inevitably mixed in.

Preferably 1 to 20 mL, and more preferably 2 to 6 mL of the aromatic hydrocarbon based solvent which has a boiling point of 140° C. or more is used for 1 g of the anhydride compound. By setting the used amount of the aromatic hydrocarbon based solvent to the range above, deposition of a mixture comprising an amide compound I and an amide compound II described later or the like can be suppressed. Furthermore, when the second reaction solution is used, if the amount of the aromatic hydrocarbon based solvent is not enough, the aromatic hydrocarbon based solvent can also be added.

In addition, the amount of the optically active amine compound is not particularly limited, and preferably 0.8 to 2.0 mol, more preferably 0.9 to 1.2 mol of the optically active amine compound is used for 1 mol of the anhydride compound.

The reaction temperature during the reaction of the anhydride compound and the optically active amine compound is preferably a temperature at which the anhydride compound to be the raw material and the mixture comprising the amide compound I and the amide compound II being generated are not deposited. Specifically, the reaction temperature is preferably 140° C. or more, and more preferably 160° C. or more. In addition, an upper limit of the reaction temperature is the reflux temperature of the reaction solution, which may be 210° C. or even be 190° C. in particular.

The reaction of the anhydride compound and the optically active amine compound is instantaneously reacted by mixing the two compounds. Therefore, the optically active amine compound is preferably mixed at the condition that the anhydride compound is not deposited in the reaction mixture. The mixing may be done by stirring and mixing the reaction mixture. That is, preferably, in the second reaction solution in which the water is removed by azeotropy, the optically active amine compound is added into the second reaction solution and be stirred and mixed at the same time under the temperature condition which the anhydride compound is not deposited.

The reaction is preferably implemented at the reflux temperature of the solution when the optically active amine compound is blended with the reaction solution (preferably the second reaction solution). On this occasion, the dehydration reaction of the mixture described later is started when the reaction ends, and the trione compound can be obtained. Therefore, the reaction is preferably implemented by the same device which produces the anhydride compound. By using the same device, the operation can be improved.

The reaction is, as mentioned above, instantaneously ended when the anhydride compound contacts with the optically active amine compound. Therefore, the reaction time may be appropriately determined by confirming the state of consumption of the anhydride compound. In addition, the reaction atmosphere is not particularly limited either, and the reaction can be implemented under the air atmosphere, or the inert gas atmosphere such as the nitrogen gas or the like. In addition, because the reaction is completed instantaneously, the reaction can be implemented under any condition of reduced pressure, ordinary pressure, and increased pressure. However, in order to directly carry out the subsequent dehydration reaction of the mixture, the implementation under reduced pressure to ordinary pressure is preferable. Above all, when the aromatic hydrocarbon based solvent is used, the reaction is preferably implemented under ordinary pressure.

According to studies of inventors of the present invention, it is found that the mixture which is obtained by the reaction of the anhydride compound and the optically active amine compound and comprises the amide compound I represented by the following formula (9)

[Formula 9]
Formula 9

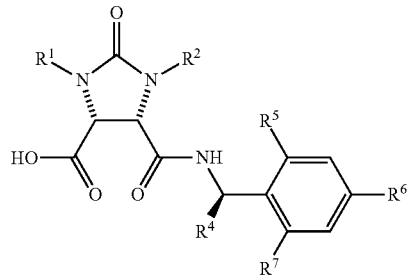

(9)

(wherein, $R^1$ and $R^2$ have the same meanings as those in the formula (11), and $R^4$, $R^5$, $R^6$, and $R^7$ have the same meanings as those in the formula (8)) and the amide compound II represented by the following formula (10)

[Formula 10]
Formula 10

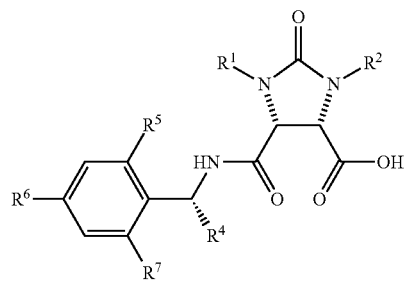

(10)

(wherein, $R^1$ and $R^2$ have the same meanings as those in the formula (11), and $R^4$, $R^5$, $R^6$, and $R^7$ have the same meanings as those in the formula (8)) is difficult to be dissolved in a solvent such as toluene. Therefore, it is found that there are occasions that crystals of the mixture are deposited in the toluene and inhibit the stirring the reaction mixture depending on the reaction conditions. On contrast, because the solubility of the mixture is high in the above-described aromatic hydrocarbon based solvent which has a boiling point of 140° C. or more, the deposition of the mixture can be suppressed and the dehydration reaction of the mixture can be promoted under uniform conditions.

(Dehydration Reaction of Mixture)

In the embodiments of the present invention, next, the mixture comprising the amide compound I and the amide compound II is dehydrated to produce the trione compound represented by the formula (1) described later. Particularly, the first reaction solution which comprises the mixture that is obtained by the reaction and comprises the amide compound I and the amide compound II, and the aromatic hydrocarbon based solvent which has a boiling point of 140° C. or more can be refluxed directly to dehydrate the mixture and obtain the trione compound. In the following, the dehydration reaction of the mixture comprising the amide compound I and the amide compound II is described.

The mixture which is obtained by the reaction and comprises the amide compound I and the amide compound II can also be temporarily taken out from the reaction mixture to implement the dehydration reaction separately. However, in order to implement the dehydration reaction in a comparatively gentle condition, for example, at a temperature (below 220° C.) lower than the known document, a method which removes water from the solution in which the mixture is dissolved is preferably adopted. In order to prepare this solution, a solvent which is the same as the aromatic hydrocarbon based solvent illustrated in the aforementioned "method for producing anhydride compound" is preferably used. Above all, in order to improve the operation to the upmost degree, the first reaction solution is preferably used.

In order to implement the dehydration reaction of the mixture in a solution dissolved uniformly, preferably 1 to 20 mL, more preferably 2 to 6 mL of the aromatic hydrocarbon based solvent is used for 1 g of the mixture (the total of the amide compound I and the amide compound II). When the first reaction solution is used, if the amount of the aromatic hydrocarbon based solvent is not enough, the aromatic hydrocarbon based solvent can also be newly added.

The dehydration reaction of the mixture is preferably carried out in a state that the reaction mixture is sufficiently mixed, and stirring and mixing is preferable. The temperature during the dehydration (the reaction temperature) is preferably the reflux temperature of the reaction solution, specifically, is preferably in a range of 140° C. or more and 210° C. or less, and more preferably in a range of 160 to 190° C. The dehydration reaction can be implemented under any condition of reduced pressure, ordinary pressure and increased pressure. However, in order to dehydrate sufficiently, the dehydration reaction is preferably implemented in the range from reduced pressure to ordinary pressure. Above all, when the aromatic hydrocarbon based solvent is used, the aromatic hydrocarbon based solvent easily forms an azeotropic mixture with water and the dehydration reaction easily proceeds, so that ordinary pressure is also acceptable.

The reaction time is not particularly limited either and may be appropriately determined by confirming the generation state of the trione compound. That is, the amount of the azeotropic water is confirmed to confirm the progress of the reaction, and the reaction may be implemented until no azeotropic water comes out. Usually, 0.5 to 20 hours is sufficient. In addition, the reaction atmosphere is not particularly limited either, and the dehydration reaction can be implemented under the air atmosphere or the atmosphere of inert gas such as nitrogen gas or the like.

In the embodiment of the present invention, in order to further improve the operation, it is preferable that the first reaction solution is used directly for dehydration. That is, the first reaction solution can be refluxed directly to make the water azeotropic with the aromatic hydrocarbon based solvent and remove the water from the reaction mixture, thereby promoting the dehydration reaction. Therefore, the reaction is preferably implemented by the same device in which the anhydride compound is reacted with the optically active amine compound. The operation can be improved by using the same device.

If the mixture, that is, the mixture comprising the amide compound I and the amide compound II, is dehydrated, both of them become the trione compound represented by the following formula (1)

[Formula 1]
Formula 1

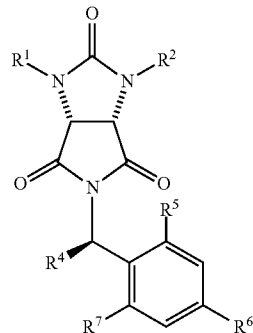

(1)

In the formula (1), $R^1$ and $R^2$ have the same meanings as those in the formula (11) and may be the same or different, and each represents a hydrogen atom or a protecting group of an ureylene group. The protecting group of the ureylene group may be an alkyl group, an aryl group, an aralkyl group, or an acyl group. Above all, the protecting group may be an alkyl group with a carbon number of 1 to 10, an aryl group with a carbon number of 5 to 10, an aralkyl group with a carbon number of 6 to 11, or an acyl group with a carbon number of 1 to 11. Particularly, each of $R^1$ and $R^2$ is preferably a benzyl group.

In addition, $R^4$ has the same meaning as in the formula (8) and represents an alkyl group, an aralkyl group, and an aryl group. Above all, an alkyl group with a carbon number of 1 to 10, an aralkyl group with a carbon number of 6 to 11, or an aryl group with a carbon number of 5 to 10 is preferable. Particularly, $R^4$ is preferably a methyl group.

$R^5$, $R^6$, and $R^7$ also have the same meanings as those in the formula (8), and each of them represent a hydrogen atom, an alkyl group, an alkoxy group, or a halogen atom. Above all, a hydrogen atom, an alkyl group with a carbon number of 1 to 10, an alkoxy group with a carbon number of 1 to 10, or a halogen atom is preferable. Particularly, each of $R^5$, $R^6$, and $R^7$ is preferably a hydrogen atom.

Above all, if the particularly preferred trione compound is illustrated, cis-1,3-dibenzyl-5-[(R)-1-phenethyl] hexahydropyrrolo [3,4-d] imidazole-2,4,6-trione is listed.

(Purification of Trione Compound)

In the embodiment of the present invention, the trione compound can be produced by the aforementioned method. The method for purifying the trione compound is not particularly limited and is preferable to adopt the following method.

Specifically, the solvent, for example, the aromatic hydrocarbon based solvent is distilled away from the reaction solution. Then, it is preferable that the residue is dissolved in a mixed solvent which comprises water and a hydrophilic solvent such as an alcohol with a carbon number of 1 to 6, a glycol with a carbon number of 1 to 6, an alkylene glycol monoalkyl ether with a carbon number of 2 to 6 or the like, and the crystals (the trione compound) are deposited. As for the mixed solvent, preferably 0.5 to 10 mL of the hydrophilic solvent and 0.5 to 10 mL of water, more preferably 2 to 6 mL of the hydrophilic solvent and 1 to 3 mL of water are used for 1 g of solid content of the residue. It is preferable that the temperature of crystallization or the like and the temperature at the time of dissolving the residue are appropriately determined by the used amount of the mixed solvent.

The crystals of the trione compound taken out as mentioned above can also be purified once again by methods such as devitrification, column separation, washing or the like.

Next, the method for reducing the trione compound to produce the amide alcohol compound is described.

(Reduction of Trione Compound (Producing Method of Amide Alcohol Compound))

In the embodiment of the present invention, the main characteristic is that the trione compound produced by a known method or the above method is (i) reduced by $NaAlH_2(OCH_2CH_2OCH_3)_2$ and subsequently further reduced by a metal borohydride salt, or (ii) reduced by calcium borohydride, thereby producing the amide alcohol compound represented by the formula (3) described later. The impurity of the optical isomer can be reduced by implementing the reduction reaction under the condition of (i) or (ii). Next, the reaction is described.

(i) Method in which the Trione Compound is Reducing by $NaAlH_2(OCH_2CH_2OCH_3)_2$ and Subsequently Further Reduced by Metal Borohydride Salt In this method, at first, the trione compound is reduced by $NaAlH_2(OCH_2CH_2OCH_3)_2$. The $NaAlH_2(OCH_2CH_2OCH_3)_2$ to be used may be a toluene solution of 60 mass % or more and 70 mass % or less, and those commercially available can be used.

(i)-1 Reduction by $NaAlH_2(OCH_2CH_2OCH_3)_2$

If the trione compound is reduced by $NaAlH_2(OCH_2CH_2OCH_3)_2$, the compound as described below is obtained. That is, an aminal compound represented by the following formula (12)

[Formula 12]
Formula 12

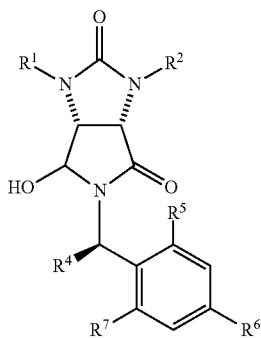

(12)

(wherein, $R^1$ and $R^2$ have the same meanings as those in the formula (11), and $R^4$, $R^5$, $R^6$, and $R^7$ have the same meanings as those in the formula (8)) (hereinafter may also be simply referred to as "the aminal compound"), and one portion of an amide aldehyde compound represented by the following formula (13)

[Formula 13]
Formula 13

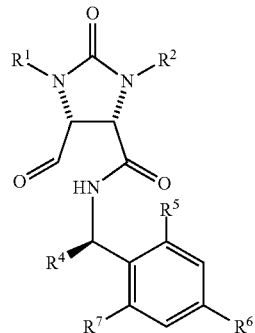

(13)

(wherein, $R^1$ and $R^2$ have the same meanings as those in the formula (11), and $R^4$, $R^5$, $R^6$, and $R^7$ have the same meanings as those in the formula (8)) (hereinafter may also be simply referred to as "the amide aldehyde compound) are obtained. However, the aminal compound and the amide aldehyde compound are in an equilibrium state and the aminal compound is in dominance, so that isolation and analysis of the amide aldehyde compound are difficult. Therefore, in the following further reduction or the like, a total amount of the aminal compound and the amide aldehyde compound is set as the standard.

If the trione compound is reduced by $NaAlH_2(OCH_2CH_2OCH_3)_2$, the aminal compound and the amide aldehyde compound can be obtained. Therefore, when these compounds are reduced by a metal borohydride salt described later, the amide alcohol compound which has few impurity of the optical isomer can be obtained.

When the trione compound is reduced by $NaAlH_2(OCH_2CH_2OCH_3)_2$, the two may contact with each other. In the case of contacting, the reaction is preferably implemented in a reaction solvent.

The reaction solvent to be used may be an aliphatic hydrocarbon, an aromatic hydrocarbon, ether, or a halogen-containing hydrocarbon or the like. Specifically, hexane, heptane, toluene, xylene, diethyl ether, t-butyl methyl ether, dibutyl ether, tetrahydrofuran, 2-methyl tetrahydrofuran, 1,2-dimethoxy ethane, 1,4-dioxane, dichloromethane, chlorobenzene or the like can be listed. These reaction solvents may be one kind or a mixture of multiple kinds of solvents. When multiple kinds of solvents are used, the amount of the reaction solvent is based on a total amount of the solvents.

The amount of the reaction solvent is not particularly limited. Above all, considering the ease of operation and a work up or the like, the amount of the reaction solvent is preferably 1 to 100 times, more preferably 3 to 20 times of 1 pts. mass of the trione compound.

The amount of $NaAlH_2(OCH_2CH_2OCH_3)_2$ is not particularly limited. In order to reliably obtain the aminal compound and the amide aldehyde compound with a good yield ratio, the amount of $NaAlH_2(OCH_2CH_2OCH_3)_2$ is preferably 1 to 10 mol, more preferably 1 to 3 mol for 1 mol of the trione compound.

In order to make $NaAlH_2(OCH_2CH_2OCH_3)_2$ contact with the trione compound, $NaAlH_2(OCH_2CH_2OCH_3)_2$ and the trione compound are preferably mixed. Particularly, it is preferable to make $NaAlH_2(OCH_2CH_2OCH_3)_2$ contact with the trione compound by mixing and stirring them in the reaction solvent. When $NaAlH_2(OCH_2CH_2OCH_3)_2$ and the trione compound are introduced into a reaction vessel and mixed in the reaction vessel, a procedure to introduce each component into the vessel is not particularly limited.

For example, each component may be introduced into the reaction vessel at the same time, or it may be that one component is introduced into the reaction vessel first, and then the other component is introduced into the reaction vessel. It is preferable that the trione compound is diluted with a solvent as necessary to be introduced into the reaction vessel first, and after the temperature is lowered, NaAlH$_2$(OCH$_2$CH$_2$OCH$_3$)$_2$ which is diluted with a solvent as necessary is added into the reaction vessel. In this way, a local reaction can be suppressed and the aminal compound and the amide aldehyde compound which have few impurities can be obtained.

From a point of highly selectively promoting the reaction, the reaction temperature at the time of reducing the trione compound by NaAlH$_2$(OCH$_2$CH$_2$OCH$_3$)$_2$ is preferably −100° C. or more and 10° C. or less, more preferably −20° C. or more and 5° C. or less.

In addition, a reaction time is not particularly limited either and may be appropriately determined by confirming a consumption amount of the trione compound which is the raw material.

The aminal compound and the amide aldehyde compound can be efficiently produced by making NaAlH$_2$(OCH$_2$CH$_2$OCH$_3$)$_2$ contact with the trione compound under the conditions as mentioned above. The next reduction reaction can be carried out directly without taking the obtained aminal compound and amide aldehyde compound out from the reaction solvent. In addition, the aminal compound and the amide aldehyde compound can also be temporarily taken out from the reaction solvent to carry out the next reduction.

(i)-2 Reduction by Metal Borohydride Salt after being Reduced by NaAlH$_2$(OCH$_2$CH$_2$OCH$_3$)$_2$ By overusing NaAlH$_2$(OCH$_2$CH$_2$OCH$_3$)$_2$ and increasing the reaction temperature or the like, the amide alcohol compound can also be obtained from the trione compound by the reduction by NaAlH$_2$(OCH$_2$CH$_2$OCH$_3$)$_2$ only. However, from a view point of production cost and promoting the reaction under mild conditions, it is preferable that after the trione compound is temporarily made into the aminal compound and the amide aldehyde compound by NaAlH$_2$(OCH$_2$CH$_2$OCH$_3$)$_2$, the aminal compound and the amide aldehyde compound are further reduced by the metal borohydride salt. The amide alcohol compound represented by the following formula (3)

[Formula 3]
Formula 3

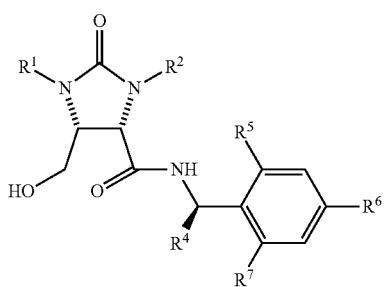

(3)

(wherein, R$^1$ and R$^2$ have the same meanings as those in the formula (11), and R$^4$, R$^5$, R$^6$, and R$^7$ have the same meanings as those in the formula (8)) can be produced by reducing the aminal compound and the amide aldehyde compound by the metal borohydride salt. Therefore, the sequence of carrying out reduction first by NaAlH$_2$(OCH$_2$CH$_2$OCH$_3$)$_2$ and then by the metal borohydride salt is very important. For example, if the reduction reaction is carried out by sodium borohydride first, the optical isomer of the amide alcohol compound tends to increase in the form of impurity as in Patent Document 1.

The metal borohydride salt is not particularly limited. Specifically, sodium borohydride, potassium borohydride, lithium borohydride, calcium borohydride and the like are listed. One kind or multiple kinds of these metal borohydride salts can be used. When multiple kinds are used, the total amount becomes the standard.

The used amount of the metal borohydride salt is not particularly limited as long as the amount is sufficient to reduce the aminal compound and the amide aldehyde compound. Above all, considering the yield ratio of the amide alcohol compound and ease of the work up or the like, the used amount of the metal borohydride salt with respect to a total of 1 mol of the aminal compound and the amide aldehyde compound is preferably 0.5 to 10 mol, more preferably 0.5 to 2 mol.

When the aminal compound and the amide aldehyde compound are brought into contact with the metal borohydride salt, it is preferable to implement the reaction in a reaction solvent. That is, it is preferable to stir and mix the two in the reaction solvent to make them contact. The reaction solvent is not particularly limited and may be a solvent which can promote the reduction reaction. Specifically, an alcohol with a carbon number of 1 to 6 such as methanol, ethanol, 1-propanol, 2-propanol, butanol, ethylene glycol, ethylene glycol monomethyl ether (2-methoxyethanol), 1-methoxy-2-propanol, 1-methyl-2-butanol or the like; and an ether such as 1,2-dimethoxy ethane or the like are more preferable. Furthermore, ethanol and 2-propanol are preferably used. Furthermore, these reaction solvents can also comprise water which is inevitably contained.

The used amount of the reaction solvent is not particularly limited either, and is preferably 0.5 to 100 times, more preferably 2 to 20 times with respect to a total of 1 pts. mass of the aminal compound and the amide aldehyde compound.

The reaction temperature at the time of bringing the aminal compound and the amide aldehyde compound into contact with the metal borohydride salt is not particularly limited and is preferably −20° C. or more and 100° C. or less, more preferably 0° C. or more and 60° C. or less.

The reaction time for reducing the aminal compound and the amide aldehyde compound is not particularly limited either, and can be appropriately determined by confirming the consumption amount of the aminal compound and the amide aldehyde compound and a generation amount of the amide alcohol compound.

According to the above method, the amide alcohol compound can be obtained with a good yield ratio by reducing the aminal compound and the amide aldehyde compound. The obtained amide alcohol compound can be taken out from the reaction mixture by a known method. Specifically, an acid is added into the reaction solution, in which the reaction is completed, to decompose excessive metal hydrides. Then, water can be added to make the crystals of the amide alcohol compound deposited and the crystals are taken out, or the reaction solvent can be concentrated to extract the amide alcohol compound by a proper solvent, and the amide alcohol compound is taken out as crystals after carrying out operations such as concentration, recrystallization, drying or the like.

(ii) Reduction by Calcium Borohydride

In conventional technologies, sodium borohydride is used to reduce the trione compound and produce the amide alcohol compound. Calcium borohydride is a substance similar to sodium borohydride, and the amount of the optical isomer can be reduced by using calcium borohydride. The reason is considered to be that calcium borohydride is reacted in a lower temperature compared with sodium borohydride.

It is considered that the aminal compound and the amide aldehyde compound are temporarily generated by performing reduction by calcium borohydride. However, it is considered that because the reaction proceeds comparatively fast in the system of the reduction reaction, the aminol compound and the amide aldehyde compound that are generated directly become the amide alcohol compound. Therefore, in the method of (ii), it is difficult to prove that the aminol compound and the amide aldehyde compound are generated. However, it is presumed, from the fact that plenty of the amide alcohol compound is obtained, that the aminol compound and the amide aldehyde compound are generated and subsequently become the amide alcohol compound. Furthermore, as shown in examples described later, when the reaction liquid is not isolated, the aminol compound can be confirmed by high-performance liquid chromatography.

The calcium borohydride can be produced as follows. For example, the calcium borohydride can be produced by making a halide of calcium and a monovalent metal salt of borohydride (for example, sodium borohydride, or potassium borohydride) react in a solvent such as an alcohol with a carbon number of 1 to 4. In the reaction, 2 mol of the "monovalent metal salt of borohydride" may be used with respect to 1 mol of the halide of calcium. Specifically, 1 mol of the calcium borohydride can be synthesized by making 2 mol of sodium borohydride react with 1 mol of calcium chloride.

After being produced by the above method, the obtained calcium borohydride can also be temporarily purified to be used, but the calcium borohydride is not stable, so that the calcium borohydride is preferably used directly without being isolated after being produced.

In order to reduce the trione compound, the trione compound may be brought into contact with the calcium borohydride.

The used amount of the calcium borohydride is not particularly limited as long as the amount is sufficient to reduce the trione compound. Above all, considering the yield ratio of the amide alcohol compound and the ease of work up or the like, the amount of the calcium borohydride with respect to 1 mol of the trione compound is preferably 1 to 10 mol, more preferably 1 to 4 mol. Furthermore, the "calcium borohydride" can be produced by the above method. At the time of producing the calcium borohydride by this method, the "calcium borohydride" which has the same number of moles as the halide of calcium used in the reaction is generated. Therefore, when the "calcium borohydride" is used without being isolated, the number of moles of the "calcium borohydride" used in the reduction may be determined using the number of moles of the halide of calcium used in the reaction as the standard.

When the trione compound is brought into contact with the calcium borohydride, it is preferable to implement in a reaction solvent. That is, it is preferable to stir and mix them in the reaction solvent to be contacted. The reaction solvent is not particularly limited, and a reaction solvent which is the same as the reaction solvent described in (i)-2 "reduction of metal borohydride salt" can be used. Above all, the alcohol with a carbon number of 1 to 6 is preferable, and above all, ethanol and 2-propanol are preferable.

The used amount of the reaction solvent is not particularly limited either, and is preferably 1 to 100 times, more preferably 2 to 20 times of 1 pts. mass of the trione compound. Furthermore, the amount of the reaction solvent may include the solvent when the calcium borohydride is generated.

The reaction temperature at the time of bringing the trione compound into contact with the calcium borohydride is not particularly limited, and is preferably −100° C. or more and 100° C. or less, more preferably −30° C. or more and 50° C. or less, further preferably −10° C. or more and 50° C. or less, and particularly preferably −10° C. or more and 40° C. or less.

The reaction time for reducing the trione compound is not particularly limited either, and may be appropriately determined by confirming the consumption amount of the aminal compound and the generation amount of the amide alcohol compound.

According to the above method, the amide alcohol compound can be obtained with a good yield ratio by reducing the trione compound. The obtained amide alcohol compound can be taken out from the reaction mixture by a known method. Specifically, an acid is added into the reaction solution, in which the reaction is completed, to decompose excessive metal hydrides. Then, water can be added to make the crystals of the amide alcohol compound deposited and the crystals are taken out, or the reaction solvent can be concentrated to extract the amide alcohol compound by a proper solvent, and the amide alcohol compound can be taken out as crystals after carrying out operations such as concentration, recrystallization, drying or the like.

The lactone compound is produced from the amide alcohol compound which is obtained in this way. Next, the producing method of the lactone compound is described specifically.

(Producing Method of Lactone Compound)

The amide alcohol compound which is obtained by the above method can be made into lactone compound by a known method. Specifically, the lactone compound represented by the following formula (4)

[Formula 4]
Formula 4

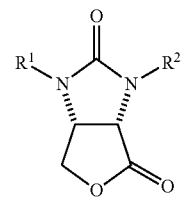

(4)

(wherein, $R^1$ and $R^2$ have the same meanings as those in the formula (11)) can be produced by cyclizing the amide alcohol compound by an acid.

The acid to be used is not particularly limited, and a known acid can be used. Specifically, hydrochloric acid, sulfuric acid, p-toluene sulfonic acid, methane sulfonic acid, phosphoric acid, and acetic acid or the like can be listed.

In order to bring the amide alcohol compound into contact with the acid, the two may be mixed. In the mixing, it is preferable to mix in a reaction solvent. The reaction solvent can use the reaction solvent illustrated in the producing method of the aminal compound.

The amount of the acid to be used is not particularly limited, and is usually 0.1 to 1000 mol with respect to 1 mol of the amide alcohol compound. In addition, the reaction temperature is not particularly limited either and is preferably −20 to 110° C.

According to the method as described above, the lactone compound can be produced. The obtained lactone compound can be taken out from the reaction mixture after carrying out operations such as extraction by a proper solvent, concentration, recrystallization, and drying or the like.

(Preferred Producing Method of Lactone Compound)

Although the lactone compound can be produced by the method as described above, in order to improve the yield ratio of the lactone compound, easily remove the reaction solvent used in the reaction, and improve the operation of a work up process, it is preferable to cyclize in the condition as follows. Specifically, it is preferable that after the amide alcohol compound represented by the formula (3) is produced, the amide alcohol compound is cyclized in the presence of hydrogen chloride in a solvent comprising an alkylene glycol monoalkyl ether in which the total number of carbon atoms in a molecule is 2 to 12, thereby producing the lactone compound.

That is, it is preferable that the amide alcohol compound is brought into contact with the hydrogen chloride in the solvent comprising an alkylene glycol monoalkyl ether in which the total number of carbon atoms in a molecule is 2 to 12, thereby cyclizing the amide alcohol compound to produce the lactone compound.

(Preferred Producing Method of Lactone Compound; Hydrogen Chloride)

The preferred producing method of the lactone compound is preferably implemented in the presence of hydrogen chloride. The hydrogen chloride to be used can be introduced into the reaction mixture in a state of hydrochloric acid comprising water, or chloride gas can be introduced into the reaction mixture. However, considering productivity and simplicity of the device, the hydrogen chloride is preferably used in the state of hydrochloric acid comprising water. When hydrochloric acid is used, the hydrochloric acid which has 30 to 40 mass % of hydrogen chloride and 60 to 70 mass % of water (wherein, a total of the water and the hydrogen chloride is 100 mass %) can be used. The hydrogen chloride or the hydrochloric acid can use those commercially available.

The used amount of the hydrogen chloride is not particularly limited, and in order to facilitate the work up process and sufficiently promote the reaction, the used amount of the hydrogen chloride is preferably 0.1 to 100 mol, more preferably 1 to 10 mol with respect to 1 mol of the amide alcohol compound.

(Preferred Producing Method of Lactone Compound; Reaction Solvent (Alkylene Glycol Monoalkyl Ether))

In the preferred producing method of the lactone compound, the cyclization reaction is carried out in the solvent comprising an alkylene glycol monoalkyl ether in which the total number of carbon atoms in a molecule is 2 to 12. By using the alkylene glycol monoalkyl ether, the reaction can proceed in a comparatively short time, the generation of by-products can be suppressed, and the work up process can be facilitated. Above all, in order to further facilitate the removal and further increase the yield ratio of the lactone compound, an alkylene glycol monoalkyl ether in which the total number of carbon atoms in a molecule is 2 to 6 is preferably used.

The alkylene glycol monoalkyl ether is preferably an alcohol represented by the following formula (A)

[Formula 14]
Formula 14

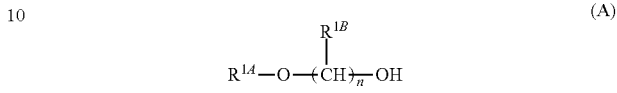

(wherein, $R^{1A}$ represents an alkyl group with a carbon number of 1 to 6, $R^{1B}$ represents a hydrogen atom, or an alkyl group with a carbon number of 1 to 6; when n is 2 or more, $R^{1B}$ can represent the same group or different groups, and n is an integer from 1 to 6). That is, in the formula (A), the total number of the number of carbon atoms of $R^{1A}$ and the number of carbon atoms in n repetition portions is 2 to 12, more preferably 2 to 6.

$R^{1A}$ represents an alkyl group with a carbon number of 1 to 6, and more preferably represents an alkyl group with a carbon number of 1 to 4.

$R^{1B}$ represents a hydrogen atom, or an alkyl group with a carbon number of 1 to 6, and more preferably represents a hydrogen atom, or an alkyl group with a carbon number of 1 to 3. In addition, when n is 2 or more, $R^{1B}$ can represent the same group or different groups. When $R^{1B}$ represents different groups, for example, one may represent a hydrogen atom, and the others may represent an alkyl group with a carbon number of 1 to 6.

In addition, n is an integer from 1 to 6, and is preferably an integer from 1 to 2.

If specific alkylene glycol monoalkyl ethers are illustrated, 2-methoxyethanol, 2-ethoxyethanol, 2-hexyloxyethanol, 2-iso-butoxyethanol, 2-phenoxyethanol, 2-methoxy-1-propanol or the like is listed. Above all, considering the yield ratio of the lactone compound, ease of handling, and ease of removal, 2-methoxyethanol, 2-butoxyethanol, 2-methoxy-1-propanol are preferably used.

In the preferred producing method of the lactone compound, the used amount of the alkylene glycol monoalkyl ether is not particularly limited, and an amount by which stirring and mixing are sufficiently carried out in the reaction mixture may be used. Above all, considering the ease of operation and ease of removal, the used amount of the alkylene glycol monoalkyl ether at 23° C. is preferably 0.5 to 20 ml, more preferably 1 to 10 ml with respect to 1 g of the amide alcohol compound.

In the preferred producing method of the lactone compound, if a main component of the reaction solvent is the alkylene glycol monoalkyl ether, the reaction solvent can also comprise other solvents in a range causing no adverse effects on cyclization reaction. For example, when the hydrogen chloride is present in the reaction mixture as hydrochloric acid, water can also be contained as reaction solvent. Besides, in addition, the solvent contained in the amide alcohol compound can be contained, or a solvent inevitably mixed can be contained. However, considering an effect of the present invention, when the reaction solvent is set to 100 vol. %, it is preferable that the alkylene glycol monoalkyl ether is set to 90 to 100 vol. %, and other solvents are set to 0 to 10 vol. %.

(Preferred Producing Method of Lactone Compound; Other Reaction Conditions)

In the preferred producing method of the lactone compound, the hydrogen chloride is brought into contact with the amide alcohol compound in the reaction solvent comprising the alkylene glycol monoalkyl ether, so that stirring and mixing is preferable. The method for introducing the amide alcohol compound, the hydrogen chloride, and the reaction solvents comprising the alkylene glycol monoalkyl ether into the reaction mixture is not particularly limited. For example, the amide alcohol compound can be dissolved in the reaction solvent, and the hydrogen chloride (the hydrochloric acid) can be added therein while stirring and mixing.

The temperature (the reaction temperature) at the time of cyclizing the amide alcohol compound to produce the lactone compound is not particularly limited, and from a point of sufficiently promoting the reaction, the temperature is preferably 10 to 200° C., more preferably 50 to 120° C.

The reaction time is not particularly limited and may be appropriately determined by confirming the consumption amount of the amide alcohol compound and the generation amount of the lactone compound. Usually, the reaction time may be 1 minute to 20 hours, and is preferably 10 minutes to 2 hours.

In addition, an atmosphere at the time of the reaction is not particularly limited either and can be any one of an air atmosphere or an inert gas atmosphere. Considering the ease of operation, it is preferable to implement under the air atmosphere. In addition, a pressure at the time of the reaction is not particularly limited either and can be any one of increased pressure, atmospheric pressure, or reduced pressure. Considering the ease of operation here too, it is preferable to implement under the atmospheric pressure.

(Preferred Producing Method of Lactone Compound; Isolation of Lactone Compound)

The method of isolation of the lactone compound is not particularly limited, and the obtained lactone compound is preferably taken out of the reaction mixture by the method below. That is, it is preferable to adopt the method in which water is added into the reaction liquid and the lactone compound is taken out as crystals therein. The amount of the water added into the reaction liquid comprising the lactone compound is not particularly limited, and in order to increase the purity of the obtained lactone compound, the total amount of the water contained in the reaction liquid is preferably 5 to 50 ml, more preferably 1 to 10 ml with respect to 1 g of the lactone compound. Furthermore, the total amount of the water also contains, for example, the water when the hydrochloric acid is used.

The temperature at the time of depositing the crystals of the lactone compound is not particularly limited, and in order to obtain a lactone compound with higher purity, the temperature is preferably 10 to 40° C., more preferably 20 to 35° C.

In prior art in which butanol is used, butanol is not easily mixed with water and phase separation may be generated. Therefore, in order to take the lactone compound out of the reaction mixture, the butanol with a high boiling point needs to be distilled away, which may be one reason for decreasing the ease of operation. In contrast, in the preferred producing method of the lactone compound, the alkylene glycol monoalkyl ether which has a high solubility with respect to water is used, so that there is no phase separation even when water is introduced into the reaction mixture, and the crystals of the lactone compound can be deposited in the reaction mixture. As a result, the lactone compound with high purity can be isolated with good operation.

The crystals of the lactone compound which is isolated may be purified and dried by a known method.

The lactone compound which is thus obtained is subjected to thiation to produce a thiolactone compound, and the biotin is produced from the thiolactone compound. The detailed description is given below.

(Producing Method of Thiolactone Compound)

The lactone compound which is obtained by the method above can be converted to the thiolactone compound by a known method. Specifically, the thiolactone compound represented by the following formula (5)

[Formula 5]
Formula 5

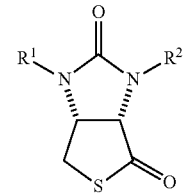

(5)

(wherein, $R^1$ and $R^2$ have the same meanings as those in the formula (11)) can be produced by reacting the lactone compound with a thiation agent.

The thiation agent to be used is not particularly limited and a known thiation agent can be used. Specifically, potassium thioacetate, potassium xanthogenate, sodium hydrosulfide, thioacetamide or the like can be listed.

In order to bring the lactone compound into contact with the thiation agent, the two may be mixed. In the mixing, it is preferable to mix in a reaction solvent. The reaction solvent can use N, N-dimethylacetamide, N, N-dimethylformamide, dimethyl sulfoxide, N-methylpyrrolidone or the like.

The amount of the thiation agent to be used is not particularly limited and may usually be 1 to 10 mol with respect to 1 mol of the lactone compound. In addition, the reaction temperature is not particularly limited either and is preferably 50 to 200° C.

The thiolactone compound can be produced according to the method as described above. The obtained thiolactone compound can be taken out from the reaction mixture after carrying out operations such as extraction by a proper solvent, concentration, recrystallization, and drying or the like.

(Producing Method of Biotin)

The thiolactone compound can be used as a raw material to produce the biotin represented by the following formula (6).

[Formula 6]
Formula 6

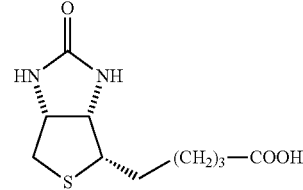

(6)

The method for producing biotin from the thiolactone compound can adopt a known method. Specifically, the production can be implemented according to the method of Patent Document 1, and Japanese Patent Publication No. S53-35076 and Japanese Patent Publication No. S55-16435, which are family patents of Patent Document 1, or the method of Japanese Patent Application Publication No. 2000-191665.

Specifically, a side chain is introduced by a Grignard reaction and dehydration and hydrogenation are performed. Then, sulfonium salt is made by hydrogen halide and is reacted with diethyl malonate and subjected to hydrolysis and decarboxylation to remove $N^1$, $N^3$-substituent, thereby producing the biotin (see Patent Document 1, Japanese Patent Publication No. S53-35076 and Japanese Patent Publication No. S55-16435).

In addition, after an addition reaction of a zinc reagent (zinc reagent: X—Zn—$CH_2$-Q-Y, in the formula, X: a halogen atom, Q: for example, a trimethylene group, Y: for example, an ester group) corresponding to the side chain with the thiolactone compound, hydrolysis and dehydration are performed. Then, reduction and deprotection reaction of $R^1$ and $R^2$ as required are performed, thereby producing the biotin (see Japanese Patent Application Publication No. 2000-191665).

The biotin can be produced by the method as described above. According to the embodiment of the present invention, the yield ratio of the amide alcohol compound, which is an intermediate of the biotin, can be improved, so that the biotin which is eventually obtained can also be efficiently produced. In addition, by producing the amide alcohol compound and the lactone compound by the preferred method mentioned in the specification, the operation can be further improved, and eventually the biotin can be produced more efficiently.

In the above, a series of producing methods for obtaining the biotin from the ureido compound is described, and in the embodiment, the series of producing methods can be divided into each unit reaction for producing the intermediate of the biotin. Next, a producing method of the intermediate of the biotin, which consists of several unit reactions, is described. Furthermore, details in the following producing method of the intermediate of the biotin are similar to details described in the above mentioned series of producing methods for obtaining the biotin.

The method of the embodiment of the present invention for producing the amide alcohol compound is characterized in that the trione compound represented by the following formula (1) is

[Formula 1]
Formula 1

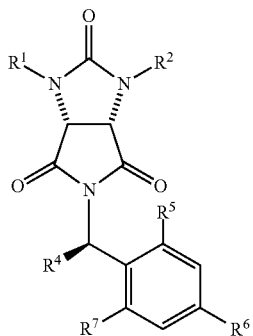

(1)

(i) reduced by $NaAlH_2$ $(OCH_2CH_2OCH_3)_2$, and subsequently further reduced by metal borohydride salt, or (ii) reduced by calcium borohydride, thereby producing the amide alcohol compound represented by the following formula (3).

[Formula 3]
Formula 3

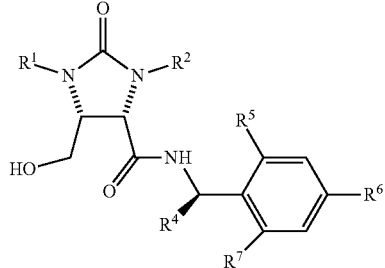

(3)

In the formulas (1) and (3), $R^1$ and $R^2$ may be the same or different and each represents a hydrogen atom or a protecting group of an ureylene group. The protecting group of the ureylene group may be an alkyl group, an aryl group, an aralkyl group, or an acyl group. Above all, an alkyl group with a carbon number of 1 to 10, an aryl group with a carbon number of 5 to 10, an aralkyl group with a carbon number of 6 to 11, or an acyl group with a carbon number of 1 to 11 is listed. Particularly, each of $R^1$ and $R^2$ is preferably a benzyl group.

In addition, $R^4$ represents an alkyl group, an aralkyl group, or an aryl group. Above all, an alkyl group with a carbon number of 1 to 10, an aralkyl group with a carbon number of 6 to 11, or an aryl group with a carbon number of 5 to 10 is preferable. Particularly, $R^4$ is preferably a methyl group.

Each of $R^5$, $R^6$, and $R^7$ represents a hydrogen atom, an alkyl group, an alkoxy group, or a halogen atom. Above all, a hydrogen atom, an alkyl group with a carbon number of 1 to 10, an alkoxy group with a carbon number of 1 to 10, or a halogen atom is preferable. Particularly, each of $R^5$, $R^6$, and $R^7$ is preferably a hydrogen atom.

According to the above mentioned producing method of the amide alcohol compound, the yield ratio of the amide alcohol compound, which is the intermediate of the biotin, can be improve by using a predefined reduction agent. Besides, the generation of the impurity of the optical isomer can be lowered when the amide alcohol compound is produced, and thus the purity of the amide alcohol compound can also be increased easily.

The method of the embodiment of the present invention for producing the lactone compound is characterized in that after producing the amide alcohol compound represented by the formula (3), the amide alcohol compound is cyclized in the presence of hydrogen chloride in a solvent comprising an alkylene glycol monoalkyl ether in which the total number of carbon atoms in a molecule is 2 to 12, thereby producing the lactone compound represented by the following formula (4)

[Formula 4]
Formula 4

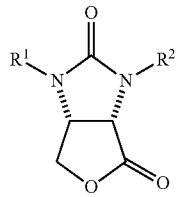

(4)

(wherein,
$R^1$ and $R^2$ have the same meanings as those in the formula (1)).

According to the above mentioned producing method of the lactone compound, the yield ratio of the lactone compound, which is the intermediate of the biotin, can be improved by using the hydrogen chloride as an acid and using a predefined alkylene glycol monoalkyl ether which is dissolved easily in water. Besides, the reaction solvent used in the reaction is easily removed, and the operation of the work up process can be improved.

The method of the embodiment of the present invention for producing the trione compound is characterized in that an anhydride compound represented by the following formula (7)

[Formula 7]
Formula 7

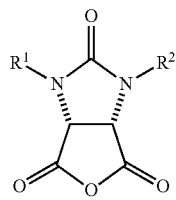

(7)

(wherein,
$R^1$ and $R^2$ have the same meanings as those in the formula (1)) is reacted with
an optically active amine compound represented by the following formula (8)

[Formula 8]
Formula 8

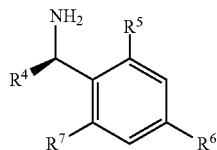

(8)

(wherein,
$R^4$, $R^5$, $R^6$, and $R^7$ have the same meanings as those in the formula (1))
in a reaction solvent comprising an aromatic hydrocarbon based solvent which has a boiling point of 140° C. or more, thereby
producing a mixture which comprises an amide compound I represented by the following formula (9)

[Formula 9]
Formula 9

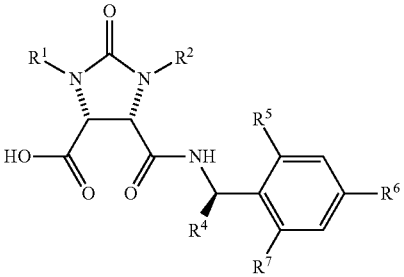

(9)

(wherein,
$R^1$, $R^2$, $R^4$, $R^5$, $R^6$, and $R^7$ have the same meanings as those in the formula (1)) and
an amide compound II represented by the following formula (10)

[Formula 10]
Formula 10

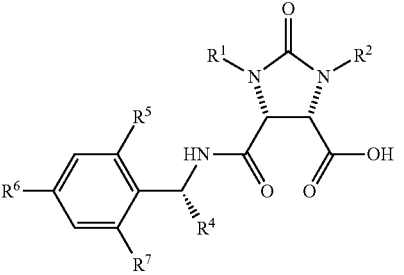

(10)

(wherein,
$R^1$, $R^2$, $R^4$, $R^5$, $R^6$, and $R^7$ have the same meanings as those in the formula (1)); and
the first reaction solution comprising the obtained mixture and the aromatic hydrocarbon based solvent which has a boiling point of 140° C. or more is refluxed to dehydrate the mixture, thereby producing the trione compound represented by the formula (1).

According to the above mentioned producing method of the trione compound, the mixture which is the intermediate of the biotin and comprises the amide compound I and the amide compound II and the trione compound can be produced with a good operation. Particularly, by using the aromatic hydrocarbon based solvent which has a boiling point of 140° C. or more from a former stage at which the ureido compound, which is used as a raw material, is made into an anhydride compound, simply by introducing the optically active amine compound into the reaction mixture and performing dehydration from the reaction mixture, the trione compound can be produced even without isolation the product every time.

EXAMPLES

Examples are listed below to specifically describe the present invention, and the examples are concrete examples to which the present invention is not limited.

Production Example 1

A reaction represented by the following formula is carried out to prepare the trione compound.

[Formula 15]
Formula 15

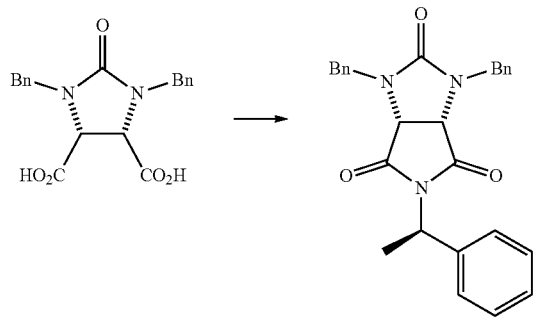

A mixture which comprises dicarboxylic acid (100 g; a compound on the left of the formula), (R)-(+)-1-methylbenzylamine (90.2 g) and o-xylene (400 mL; a boiling point of xylene is 144.4° C.) is heated to reflux for 10 hours. After the reaction liquid is distilled away under reduced pressure, the residue is heated at 220° C. for 1 hour, 2-propanol is added after heating for crystallization, and the concentration residue is filtrated, thereby obtaining a trione compound (a compound on the right of the formula: 112 g, 90%). A melting point (mp) of the trione compound is 157 to 159° C.

Example 1

(i)-1 Reduction by $NaAlH_2$ $(OCH_2CH_2OCH_3)_2$

Next, the trione compound produced by production example 1 is used to produce an aminal compound represented by the following formula under conditions below.

[Formula 16]
Formula 16

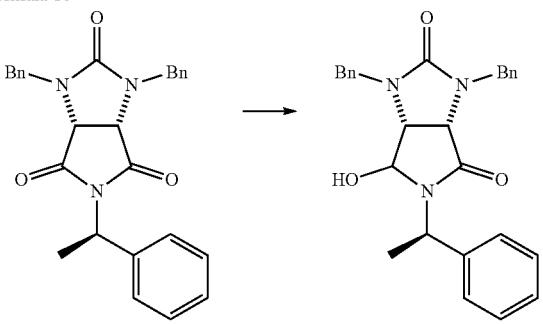

A toluene solution of $NaAlH_2(OCH_2CH_2OCH_3)_2$ (70 wt %, 866 mg) is added into a tetrahydrofuran: THF (10 mL) solution of the trione compound (1.32 g) at −10° C. After stirring the mixture for 5 hours at this temperature, an aq. ammonium chloride solution is added into the reaction liquid and the reaction is stopped. The product is extracted with ethyl acetate, washed with water, dried, and concentrated under reduced pressure, thereby obtaining the aminal compound (1.26 g, 95%) in a form of an oily matter.

MS (mass analysis): 442 (M⁺+1).
IR (KBr): ν 3332, 1699 cm⁻¹

$^1$H-NMR (400 MHz, $CDCl_3$): δ 7.35-6.99 (m, 15H), 5.38-5.32 and 5.28-5.22 (m, 1H), 5.12-5.02 (m, 2H), 4.78-4.72 and 4.40-4.35 (m, 1H), 4.06-4.00 (m, 1H), 3.88-3.83 (m, 1H), 3.75-3.65 (m, 2H), 1.80-1.60 (m, 3H).

(i)-2 Reduction by Metal Borohydride Salt

Next, the aminal compound is reduced to produce an amide alcohol compound of the following formula under conditions below.

[Formula 17]
Formula 17

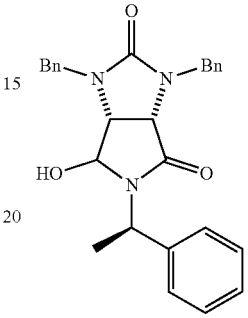

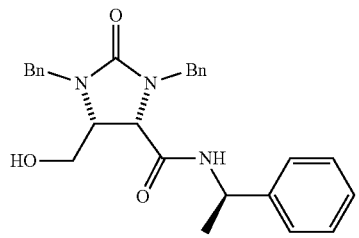

The aminal compound (1.32 g) which is produced by carrying out the same operations as the method above is dissolved in 2-propanol (13 mL), and sodium borohydride (113 mg) is added and stirred and mixed at 40° C. for 10 hours. After the reaction is completed, 5 wt % of hydrochloric acid (4 mL) is slowly added into the reaction mixture below 20° C. The amide alcohol compound (998 mg, 75%) is obtained by filtrating the solids formed. The melting point (mp) of the obtained amide alcohol compound is 113 to 116° C., and MS is 444 (M++1).

Example 2

(ii) Reduction by Calcium Borohydride

The trione compound which is produced by production example 1 is reduced under conditions shown below to produce the amide alcohol compound.

[Formula 18]
Formula 18

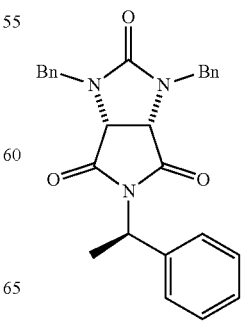

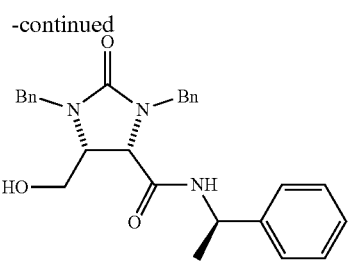

Calcium chloride (333 mg; 3 mmol) is suspended in 2-propanol (13 mL), and sodium borohydride (227 mg; 6 mmol) is added at −10° C. (calcium borohydride; 3 mmol is generated). After stirring for 30 minutes at this temperature, the trione compound (1.32 g: 3 mmol) which is obtained by production example 1 is added at −10° C. The reaction mixture is stirred and mixed at −10° C. for 5 hours and is slowly raised to 40° C., and further stirred at 40° C. for 5 hours. When an area ratio of each component of the reaction mixture is confirmed by high-performance liquid chromatography (HPLC), a conversion ratio of the trione compound to the amide alcohol is 95%, the amide alcohol compound of a target product/an isomer of the target product (simply referred to as "the isomer ratio" hereinafter) is 75/25, and the aminal compound which is the intermediate is 0.6%.

After the reaction is completed, 5 wt % of hydrochloric acid (4 mL) is slowly added at a temperature below 20° C. The amide alcohol compound (931 mg, 70%) is obtained by filtrating the crystals formed. The melting point of the obtained amide alcohol compound is 113-116° C., and MS is 444(M++1).

Example 3 (Production of Lactone Compound)

The lactone compound is produced under conditions below according to a reaction formula shown below.

[Formula 19]
Formula 19

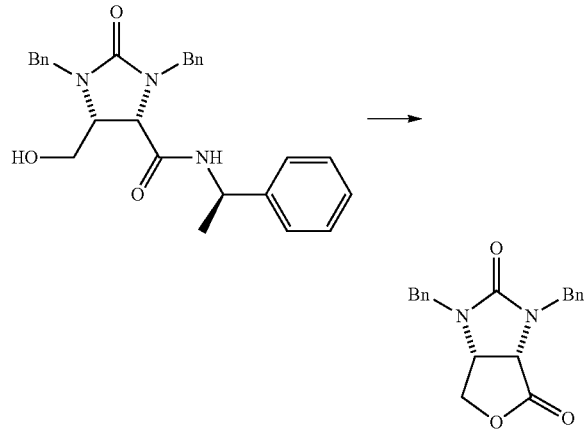

The amide alcohol compound (1.33 g) which is produced by carrying out the same operations as example 1 is suspended in 1,4-dioxane (5 mL), concentrated hydrochloric acid (0.5 mL) is added and the liquid is heated to reflux for 5 hours. After the reaction, the reaction mixture is washed by water and concentrated after being cooled to room temperature, thereby the lactone compound (967 mg, quant) is obtained. mp is 115 to 120° C.

Example 4 (Production of Thiolactone Compound)

The thiolactone compound is produced under conditions below according to a reaction formula below.

[Formula 20]
Formula 20

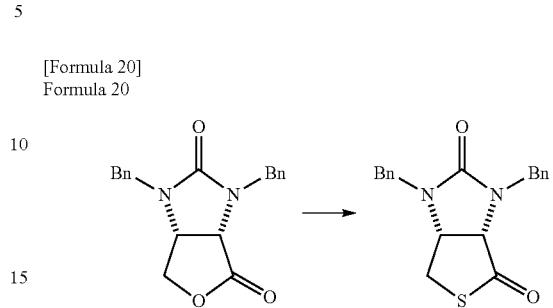

Potassium thioacetate (1.52 g) is added into a N, N-dimethyl acetamide (5 mL) solution of the lactone compound (3.22 g) which is produced by carrying out the same operations as example 3, and the solution is stirred and mixed at 150° C. for 1 hour. After the reaction is completed, water (17 mL) is added at 60° C. and the solution is slowly cooled to room temperature, and then the solution is stirred and mixed below 10° C. for 1 hour. Solids obtained after filtration are recrystallized from methanol to obtain the thiolactone compound (2.87 g, 85%). mp is 126° C.

Example 5 (Production of Biotin)

Biotin is produced under conditions below according to a reaction formula below.

[Formula 21]
Formula 21

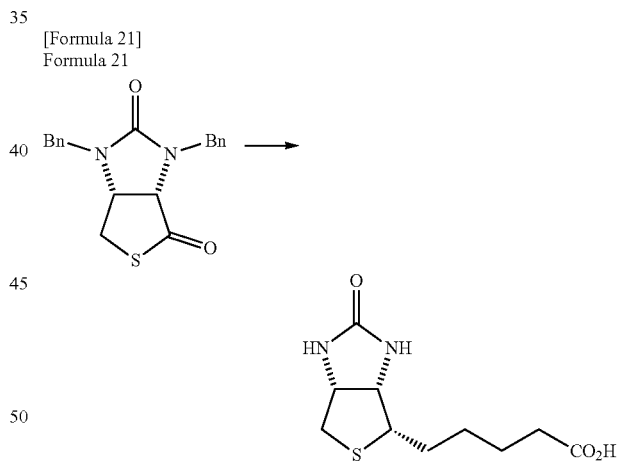

Bromine (5.8 g) is added below 40° C. into a suspension of zinc dust (9.3 g) in THF (18 mL) and toluene (12 ml). Then, 5-iodopentanoic acid ethyl ester (18.6 g) is added over 1 hour. After stirring the mixture at this temperature for 1 hour, the thiolactone compound (17.6 g) produced by carrying out the same operations as example 4, toluene (36 mL), dimethylformamide DMF (4.4 mL) and 10 wt % of Pd/C (0.5 g) are added and stirring is continued at a temperature range of 28° C. to 40° C. for 5 hours. After the reaction is completed, 18 wt % of aqueous hydrochloric acid (34 mL) is added into the reaction mixture, and the reaction mixture is stirred and mixed at room temperature for 1 hour. An organic layer is concentrated under reduced pressure after being separated, washed by water and dried.

The concentrated residue is dissolved in a mixture liquid of methanol (160 ml) and water (44 mL), and Pd (OH)$_2$/C (50 wt % wet, 1.6 g) is added to carry out contact reduction at 110° C. under a hydrogen pressure of 0.9 MPa for 12 hours. After the reaction is completed, the reaction solution is filtrated, and a filtration solution is added with 31 mass % of an aqueous solution of NaOH (19 g) and is stirred and mixed at 40° C. for 2 hours.

After the hydrogenation reaction is completed, 10 wt % of hydrochloric acid is added to the reaction liquid to reach pH1. The methanol is distilled away under reduced pressure, and the product is extracted by ethyl acetate, washed by water and concentrated.

Methanesulfonic acid (1.2 g) and mesitylene (1.2 mL) are added to the concentrated residue, and stirring is carried out at 135° C. for 3 hours. The reaction liquid is separated after being cooled to 85° C., and a lower layer is poured into water (8 ml). After this mixture is stirred and mixed below 10° C. for 1 hour, crystals formed are filtrated, thereby obtaining the biotin (10.7 g, 85%). mp is 231 to 232° C.

Production Example 2

Production example 2 is an example when the trione compound is produced inside the same reaction vessel from an ureido compound represented by the formula below.

[Formula 22]
Formula 22

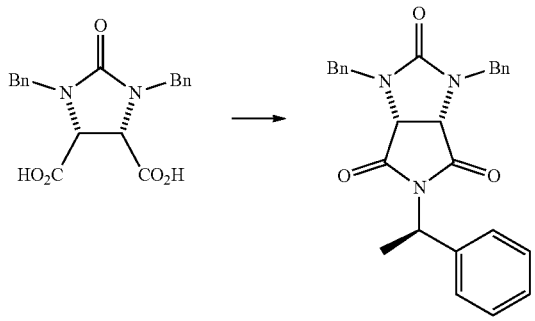

(Method for Producing Anhydride Compound from Ureido Compound; Dehydration Reaction)

Cis-1,3-dibenzyl-2-oxo-4,5-imidazolidine dicarboxylic acid (200.0 g, 564.4 mmol, ureido compound) and mesitylene (600.0 mL; the boiling point is 165° C., the "aromatic hydrocarbon based solvent which has a boiling point of 140° C. or more" of the present invention) are placed in a 3-neck round flask. A Dean-Stark tube and a condenser are installed on the 3-neck round flask, nitrogen is flowed for 1 minute to continued nitrogen substitution. Heating, refluxing, and stirring are carried out at 185° C. Water remained in the Dean-Stark tube is removed timely. The heating is carried out for 3 hours or more in total. Proceeding of the reaction is assayed (confirm that the anhydride compound is synthesized) by HPLC (high-performance liquid chromatography) using a sample to which methanolysis treatment is performed, in which 0.1 to 0.2 mL of the reaction liquid is extracted, 2 mL of methanol is added, and a few drops of 5M of NaOMe methanol liquid is further added. The second reaction solution comprising the aromatic hydrocarbon based solvent which has a boiling point of 140° C. or more and the anhydride compound is prepared by this dehydration reaction. The second reaction solution comprises 3 mL of mesitylene for every 1 g of the anhydride compound.

(Reaction Between Anhydride Compound and Optically Active Amine Compound)

A dropping funnel is installed on the 3-neck round flask, and (R)-(+)-1-methylbenzylamine (65.6 g, 536.2 mmol, 0.95 equivalent amount, optically active amine compound) is placed in the 3-neck round flask. That is, the optically active amine compound is dropped into the second reaction solution with 2 hours and 30 minutes while the second reaction solution is heated to 185° C. and stirred. The reaction is completed instantaneously. The consumption of the anhydride compound (the generation of the mixture comprising the amide compound I and the amide compound II) is confirmed by HPLC (high-performance liquid chromatography). In addition, at this time, the mixture comprising the amide compound I and the amide compound II is not deposited in the solution. The first reaction solution comprising the mixture and mesitylene is prepared by using the method above. At this time, the first reaction solution comprises 3 mL of mesitylene for every 1 g of the mixture.

(Dehydration Reaction of Mixture)

After the dropping of the optically active amine compound is stopped, the first reaction solution is further heated for 3 hours and 30 minutes while stirring. Then, it is confirmed that there is no more water remaining in the Dean-Stark tube. The consumption of the substrate (the generation of the trione compound) is substantiated by HPLC (high-performance liquid chromatography).

(Isolation and Purification of Trione Compound)

Then, a total of 200 mL of the mesitylene is extracted from the Dean-Stark tube. The temperature inside the reaction vessel is reduced to a temperature below 100° C. 700 mL of isopropyl alcohol is added while stirring. 280 mL of water is further dropped while the temperature is maintained at 80° C. Then, seed crystal is added and 220 mL of water is further added. Then, the liquid is gradually cooled to 23° C. and stirred for 24 hours, and formed crystals are filtered.

The crystals which are obtained by filtration are washed by a mixture cooled to 5° C. or less which comprises 75 mL of the isopropyl alcohol and 25 mL of water. 205.2 g of a target trione compound is obtained by vacuum-drying the washed crystals at 60° C. for 23 hours and 30 minutes (466.9 mmol, the yield is 87%). mp: 157° C., IR (KBr): 1780, 1705, 1680 cm$^{-1}$.

Reference Production Example 1

Cis-1,3-dibenzyl-2-oxo-4,5-imidazolidinedicarboxylic acid (20.0 g, 56.4 mmol, ureido compound) and toluene (80 mL) are placed in a 3-neck round flask. A Dean-Stark tube and a condenser are installed on the 3-neck round flask, and nitrogen is flowed for 1 minute to carry out nitrogen substitution. Heating, refluxing, and stirring are performed at 110° C. Water remained in the Dean-Stark tube is removed timely. Heating is performed for 10 hours or more in total. At this point, a great amount of the anhydride compound is deposited and stirring becomes difficult.

The anhydride compound which is obtained by the method above and the (R)-(+)-1-methylbenzylamine (optically active amine compound) are reacted under conditions below. The anhydride compound (50 g) is suspended in toluene (20 mL), (R)-(+)-1-methylbenzylamine (18.9 g) is added and reflux dehydration is performed at 110° C. using the Dean-Stark tube. After 2 hours elapsed, the crystals of the mixture comprising the amide compound I and the amide compound II are deposited in the reaction solution, and stirring becomes difficult.

Comparison Example 1

The trione compound (1 g; 2.28 mmol) which is obtained by production example 2 is dissolved in ethanol (500 mL), sodium borohydride (2.28 mmol; 0.19 g (purity 90%)) is filled into the reaction mixture under ice cooling, and stirring is performed at a reaction temperature of 23° C. for 16 hours. Then, the reaction temperature is set to 50° C. and stirring and mixing are performed for 2 hours. The obtained reaction solution is analyzed by HPLC. The conversion ratio of the trione compound is 100%, the isomer ratio is 61/39, and the aminal compound is 0%.

Example 6

Except that the trione compound obtained by production example 2 is used, same operations as example 2 are carried out. The yield ratio of the obtained amide alcohol compound or the like is same as example 2.

Example 7 (Reduction by Calcium Borohydride)

Calcium chloride (68.26 mmol, 7.97 g (purity 95%)) and ethanol (180 mL, purity 99.4%) are added into a round flask and are dissolved using ultrasonication. The flask is subjected to ice bath and stirring is performed for 5 minutes or more. Sodium borohydride (136.51 mmol, 5.74 g (purity 90%)) is added as the flask is cooled by ice bath. Stirring is performed in the state of ice bath for 20 minutes to produce calcium borohydride.

Then, the trione compound (30.0 g, 68.26 mmol) produced by the method mentioned in production example 2 is employed, and stirring is performed at room temperature (23° C.) for 16 hours. The temperature is raised to 50° C. to perform 2 hours of stirring. The obtained reaction mixture is analyzed by HPLC. The conversion ratio of the trione compound is 100%, the isomer ratio is 75/25, and the aminal compound is 0.6%.

Water (270 mL) and acetic acid (15 mL) are added into the reaction liquid. The reaction liquid is filtered. The obtained solid is vacuum-dried at 60° C. for 6 hours or more. The amide alcohol compound is obtained by recrystallizing the product by aqueous methanol (yield: 18.8 g, yield 62%).

Example 8 (Reduction by Calcium Borohydride)

Operations the same as example 7 are carried out except that after the trione compound is filled, the reaction temperature is set to 23° C. and the reaction time is set to 16 hours in example 7. As for the result which is obtained by analysing the obtained reaction liquid by HPLC, the conversion ratio of the trione compound is 100%, the isomer ratio is 78/22, and the aminal compound is 3.4%.

Example 9 (Reduction by Calcium Borohydride)

Operations the same as example 7 are carried out except that the quantity of the calcium chloride (204.78 mmol, 23.91 g (purity 95%)) and the sodium borohydride (409.53 mmol, 17.22 g (purity 90%)) is different, the reaction temperature is set to 23° C. and the reaction time is set to 16 hours at room temperature in example 7. As for the result which is obtained by analysing the obtained reaction liquid by HPLC, the conversion ratio of the trione compound is 100%, the isomer ratio is 75/25, and the aminal compound is 2.4%.

Example 10 (Reduction by Calcium Borohydride)

Operations the same as example 7 are carried out except that the quantity of the calcium chloride (136.52 mmol, 15.94 g (purity 95%)) and the sodium borohydride (273.02 mmol, 11.48 g (purity 90%)) is different, the reaction temperature is set to 23° C., and the reaction time is set to 16 hours at room temperature in example 7. As for the result which is obtained by analysing the obtained reaction liquid by HPLC, the conversion ratio of the trione compound is 100%, the isomer ratio is 80/20, and the aminal compound is 4.95%.

Example 11 (Reduction by Calcium Borohydride)

Operations the same as example 10 are carried out except that the reaction temperature is set to room temperature (23° C.), the reaction time is set to 16 hours, then the reaction temperature is set to 50° C., and the reaction time is set to 2 hours in example 10. As for the result which is obtained by analysing the obtained reaction liquid by HPLC, the conversion ratio of the trione compound is 100%, the isomer ratio is 77/23, and the aminal compound is 0.51%.

Example 12 (Reduction by Calcium Borohydride)

Operations the same as example 7 are carried out except that the quantity of the calcium chloride (51.20 mmol, 5.98 g (purity 95%)) and the sodium borohydride (102.38 mmol, 4.305 g (purity 90%)) is different, the reaction temperature is set to room temperature of 23° C. and the reaction time is set to 16 hours in example 7. As for the result which is obtained by analysing the obtained reaction liquid by HPLC, the conversion ratio of the trione compound is 98%, the isomer ratio is 78/22, and the aminal compound is 7.65%.

Example 13 (Reduction by Calcium Borohydride)

Operations the same as example 12 are carried out except that the reaction temperature is set to room temperature (23° C.), the reaction time is set to 16 hours, then the reaction temperature is set to 50° C., and the reaction time is set to 2 hours in example 12. As for the result which is obtained by analysing the obtained reaction liquid by HPLC, the conversion ratio of the trione compound is 99%, the isomer ratio is 77/23, and the aminal compound is 4.94%.

Example 14 (Reduction by Calcium Borohydride)

Operations the same as example 7 are carried out except that the quantity of the calcium chloride (34.13 mmol, 3.99 g (purity 95%)) and the sodium borohydride (68.25 mmol, 2.87 g (purity 90%)) is different, the reaction temperature is set to room temperature of 23° C., and the reaction time is set to 16 hours in example 7. As for the result which is obtained by analysing the obtained reaction liquid by HPLC, the conversion ratio of the trione compound is 99%, the isomer ratio is 80/20, and the aminal compound is 16.83%.

Example 15 (Reduction by Calcium Borohydride)

Operations the same as example 14 are carried out except that the reaction temperature is set to room temperature (23°

C.), the reaction time is set to 16 hours, then the reaction temperature is set to 50° C., and the reaction time is set to 2 hours in example 14. As for the result which is obtained by analysing the obtained reaction liquid by HPLC, the conversion ratio of the trione compound is 99%, the isomer ratio is 80/20, and the aminal compound is 16.83%.

Results of example 6 and examples 7 to 15 are gathered in table 1.

Example 19

Operations the same as example 7 are carried out except that 2-methoxyethanol is used in place of the ethanol in example 7. As for the result which is obtained by analysing the reaction liquid by HPLC, the conversion ratio of the trione compound is 100%, the isomer ratio is 75/25, and the aminal compound is 7.88%.

TABLE 1

|  | mole ratio of trione compound/ calcium borohydride | reaction temperature · reaction time | conversion (%) | isomer ratio | aminal compound (%) |
|---|---|---|---|---|---|
| comparison example 1 | 1/1 | 23° C., 16 hours 50° C., 2 hours | 100 | 61/39 | 0 |
| example 6 | 1/1 | −10° C., 5 hours 40° C., 5 hours | 95 | 75/25 | 0.6 |
| example 7 | 1/1 | 23° C., 16 hours 50° C., 2 hours | 100 | 75/25 | 0.6 |
| example 8 | 1/1 | 23° C., 16 hours | 100 | 78/22 | 3.4 |
| example 9 | 1/3 | 23° C., 16 hours | 100 | 75/25 | 2.4 |
| example 10 | 1/2 | 23° C., 16 hours | 100 | 80/20 | 4.95 |
| example 11 | 1/2 | 23° C., 16 hours 50° C., 2 hours | 100 | 77/23 | 0.51 |
| example 12 | 1/0.75 | 23° C., 16 hours | 98 | 78/22 | 7.65 |
| example 13 | 1/0.75 | 23° C., 16 hours 50° C., 2 hours | 99 | 77/23 | 4.94 |
| example 14 | 1/0.5 | 23° C., 16 hours | 99 | 80/20 | 16.83 |
| example 15 | 1/0.5 | 23° C., 16 hours 50° C., 2 hours | 99 | 80/20 | 16.83 |

*Comparison example 1 is an example using sodium borohydride.

Example 16

Operations the same as example 7 are carried out except that n-propanol is used in place of the ethanol in example 7. As for the result which is obtained by analysing the reaction liquid by HPLC, the conversion ratio of the trione compound is 100%, the isomer ratio is 75/25, and the aminal compound is 6.94%.

Example 17

Operations the same as example 7 are carried out except that 1-methoxy-2-propanol is used in place of the ethanol in example 7. As for the result which is obtained by analysing the reaction liquid by HPLC, the conversion ratio of the trione compound is 100%, the isomer ratio is 70/30, and the aminal compound is 0.05%.

Example 18

Operations the same as example 7 are carried out except that 1-methyl-2-butanol is used in place of the ethanol in example 7. As for the result which is obtained by analysing the reaction liquid by HPLC, the conversion ratio of the trione compound is 100%, the isomer ratio is 80/20, and the aminal compound is 8.63%.

Results of the above example 7 and examples 16 to 19 are gathered in table 2 with comparison example 1 for a reference.

TABLE 2

|  | solvent | conversion (%) | isomer ratio | aminal compound (%) |
|---|---|---|---|---|
| example 16 | n-propanol | 100 | 75/25 | 6.94 |
| example 17 | 1-methoxy-2-propanol | 100 | 70/30 | 0.05 |
| example 18 | 1-methyl-2-butanol | 100 | 80/20 | 8.63 |
| example 19 | 2-methoxy ethanol | 100 | 75/25 | 7.88 |
| example 7 | ethanol | 100 | 75/25 | 0.6 |
| comparison example 1 | ethanol | 100 | 61/39 | 0 |

*Comparison example 1 is an example using sodium borohydride.

Example 20 (Production of Lactone Compound)

Operations the same as example 7 are carried out, and the obtained amide alcohol compound is used to carry out the reaction below.

[Formula 23]
Formula 23

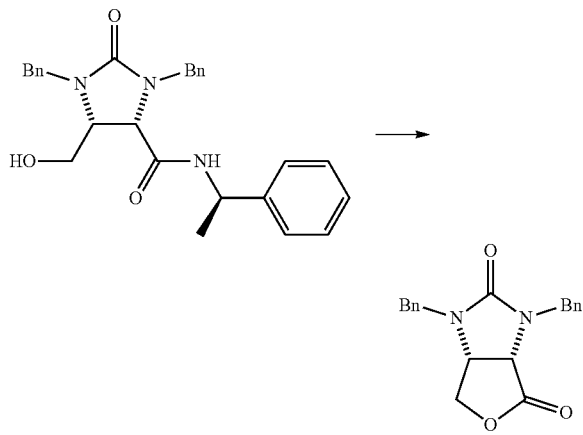

The amide alcohol compound (235.0 g, water content 17 wt %, 440 mmol), which is obtained by carrying out the operations the same as example 7, 940 mL of 2-methoxyethanol which is used as an alkylene glycol monoalkyl ether, and 36 mass % of hydrochloric acid (115.9 g, hydrogen chloride 1140 mmol, 2.6 mol is used with respect to 1 mol of the amide alcohol compound) are placed in a 3-neck round flask.

The 3-neck round flask is put into a preheated oil bath to be heated. Stirring is performed at an inner temperature of 105° C. for 10 minutes. The mixture is cooled to 25° C.-30° C. while being stirred, and water (940 mL) is slowly added for more than 5 minutes, after which stirring is performed for one night at room temperature (25° C.) to make the lactone compound represented by the formula above deposited in the reaction liquid. The reaction mixture is filtered by a glass filter funnel to obtain crystals of the lactone compound. Water (200 mL) is added to the obtained crystals and agitation and filtering are performed. The same operations are carried out for 6 times to wash the crystals. At last, water (600 mL) is added to the crystals and agitation and filtering are performed. A difference between pH of the filtrate and pH of the water used in the washing is confirmed to be below 0.5. The obtained crystals are vacuum-dried at 80° C. for 1 day. 136.5 g of the target lactone compound is obtained (423.5 mmol, yield 96%).

The analysis values of the obtained lactone compound are mp: 100 to 101° C. and IR (Nujol): 1775 $cm^{-1}$, which can confirm that the obtained lactone compound is the target lactone compound.

Example 21 (Production of Lactone Compound)

The reaction the same as example 20 is carried out. The amide alcohol compound the same as example 20 (the amide alcohol compound produced by the method the same as example 7; 5.00 g, water content 17%, 9.4 mmol), 2-butoxyethanol (20 mL) used as an alkylene glycol monoalkyl ether, and 36 wt % of hydrochloric acid (2.47 g, hydrogen chloride 24 mmol, 2.6 mol is used with respect to 1 mol of the amide alcohol compound) are placed in a 3-neck round flask.

The 3-neck round flask is put into a preheated oil bath to be heated. Stirring is performed at an inner temperature of 105° C. for 1 hour. The liquid is cooled to 30° C. while being stirred, water (40 mL) is slowly added for more than 5 minutes, and stirring is performed for one night at room temperature (25° C.) to make crystals of the lactone compound represented by the formula above deposited in the reaction liquid.

The reaction liquid is filtered by a glass filter funnel to obtain the crystals. Water (50 mL) is added to the obtained crystals, and agitation and filtering are performed. Water (100 mL) is further added, and the crystals and the water are agitated and filtered. The obtained crystals are vacuum-dried at 80° C. for 1 day. 2.30 g of the target lactone compound is obtained (7.14 mmol, yield 76%).

The analysis values of the obtained lactone compound are mp: 99 to 101° C. and IR (Nujol): 1775 $cm^{-1}$, which can confirm that the obtained lactone compound is the target lactone compound.

Example 22 (Production of Lactone Compound)

The reaction the same as example 20 is carried out. The amide alcohol compound the same as example 20 (the amide alcohol compound produced by the method the same as example 7; 4.15 g, 9.4 mmol), 2-methoxy-1-propanol (8.3 mL) used as an alkylene glycol monoalkyl ether, and 36 mass % of hydrochloric acid (2.07 g, hydrogen chloride 20.4 mmol, 2.2 mol is used with respect to 1 mol of the amide alcohol compound) are placed in a 3-neck round flask.

The 3-neck round flask is put into a preheated oil bath to be heated. Stirring is performed at an inner temperature of 100° C. for 15 minutes. The liquid is cooled to 30° C. while being stirred, water (83 mL) is slowly added for more than 5 minutes, and stirring is performed for 2 hours at room temperature (25° C.) to make crystals of the lactone compound represented by the formula above deposited in the reaction liquid.

The reaction liquid is filtered by a glass filter funnel to obtain the crystals. Water (20 mL) is added to the obtained crystals, and agitation and filtering are performed. The obtained crystals are dried by blowing air at 60° C. for 17 hours. 2.96 g of the target lactone compound is obtained (9.18 mmol, yield 98%).

The analysis values of the obtained lactone compound are mp: 100 to 101° C. and IR (Nujol): 1775 $cm^{-1}$, which can confirm that the obtained lactone compound is the target lactone compound.

Reference Production Example 2 (Production of Lactone Compound)

The reaction the same as example 20 is carried out. The amide alcohol compound the same as example 20 (the amide alcohol compound produced by the method the same as example 7; 40.00 g, 90 mmol), butanol (400 mL), and 36 mass % of hydrochloric acid (93.5 g, hydrogen chloride 900 mmol, 10 mol is used with respect to 1 mol of the amide alcohol compound) are placed in a 3-neck round flask.

Stirring is performed at an inner temperature of 110° C. for 4 hours. After the reaction is completed, 6N of an aqueous solution of NaOH (90 mL) is added into the reaction liquid for neutralization. Liquid separation is performed on the obtained mixture and an organic layer is concentrated under reduced pressure after being waterwashed. The concentrated residue is extracted by ethyl acetate, and is again concentrated under reduced pressure after being water-washed. The concentrated residue is not crystallized, so that 20 g (68%) of the target lactone compound is obtained by purifying the concentrated residue by silica gel column chromatography (elution solvent:hexane/ethyl acetate=3:1).

What is claimed is:

1. A method for producing a lactone compound in which an ureido compound represented by the following formula (11)

[Formula 11]
Formula 11

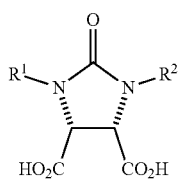

(11)

wherein, $R^1$ and $R^2$ may be the same or different and represent a hydrogen atom or a protecting group of an ureylene group, is dehydrated by refluxing in a reaction solvent comprising mesitylene, thereby producing an anhydride compound represented by the following formula (7)

[Formula 7]
Formula 7

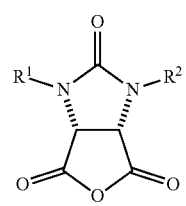

(7)

the anhydride compound and an optically active amine compound represented by the following formula (8)

[Formula 8]
Formula 8

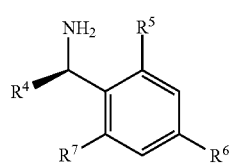

(8)

wherein, $R^4$ represents an alkyl group, an aralkyl group, or an aryl group, and each of $R^5$, $R^6$, and $R^7$ represents a hydrogen atom, an alkyl group, an alkoxy group, or a halogen atom, are reacted in a reaction solvent comprising mesitylene, thereby producing a mixture which comprises an amide compound I represented by the following formula (9)

[Formula 9]
Formula 9

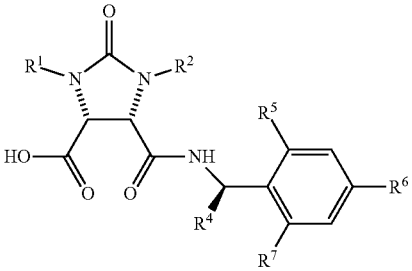

(9)

and an amide compound II represented by the following formula (10)

[Formula 10]
Formula 10

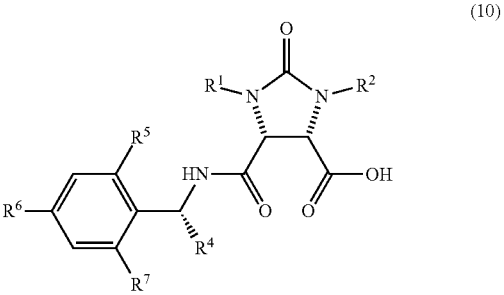

(10)

a first reaction solution comprising the obtained mixture and mesitylene is refluxed to dehydrate the mixture, thereby producing a trione compound represented by the following formula (1)

[Formula 1]
Formula 1

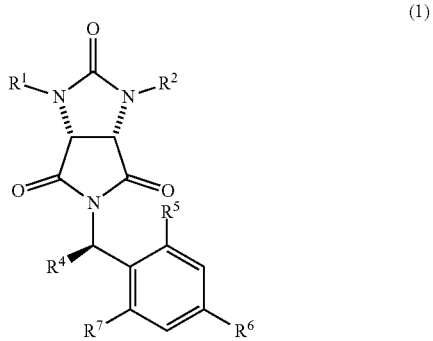

(1)

the trione compound is (ii) reduced by calcium borohydride in ethanol, thereby producing an amide alcohol compound represented by the following formula (3)

[Formula 3]
Formula 3

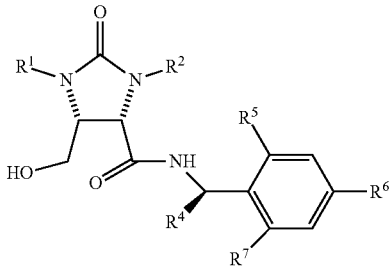
(3)

and the amide alcohol compound is cyclized in the presence of hydrogen chloride in a solvent comprising an alkylene glycol monoalkyl ether in which the total number of carbon atoms in a molecule is 2 to 12, thereby producing a lactone compound represented by the following formula (4)

[Formula 4]
Formula 4

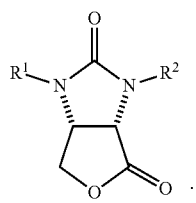
(4)

2. A method for producing an amide alcohol compound in which a trione compound represented by the following formula (1)

[Formula 1]
Formula 1

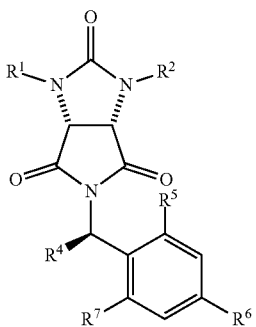
(1)

wherein, $R^1$ and $R^2$ may be the same or different and each represents a hydrogen atom or a protecting group of an ureylene group;
$R^4$ represents an alkyl group, an aralkyl group, or an aryl group; and
each of $R^5$, $R^6$, and $R^7$ represents a hydrogen atom, an alkyl group, an alkoxy group, or a halogen atom is
(ii) reduced by calcium borohydride in ethanol, thereby producing an amide alcohol compound represented by the following formula (3)

[Formula 3]
Formula 3

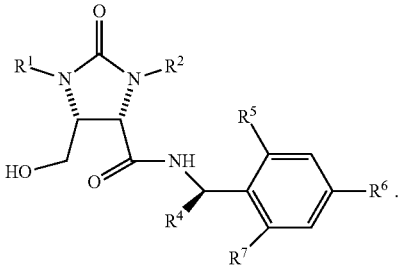
(3)

3. A method in which
an amide alcohol compound represented by the formula (3) is produced by the method according to claim 2, and
subsequently the amide alcohol compound is cyclized in the presence of hydrogen chloride in a solvent comprising an alkylene glycol monoalkyl ether in which the total number of carbon atoms in a molecule is 2 to 12, thereby producing a lactone compound represented by the following formula (4)

[Formula 4]
Formula 4

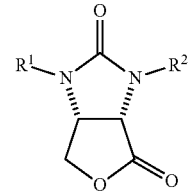
(4)

4. A method in which
a lactone compound represented by the formula (4) is produced by the method according to claim 3, and
subsequently the lactone compound is reacted with a thiation agent, thereby producing a thiolactone compound represented by the following formula (5)

[Formula 5]

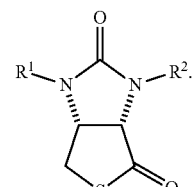
(5)

5. A method in which
after producing a thiolactone compound represented by the formula (5) by the method according to claim 4,
the thiolactone compound is used as a raw material to produce biotin represented by the following formula (6)

[Formula 6]
Formula 6

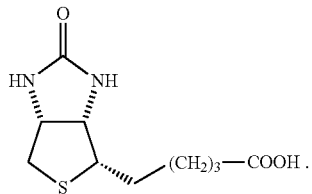
(6)

6. The method according to claim 2, wherein an anhydride compound represented by the following formula (7)

[Formula 7]
Formula 7

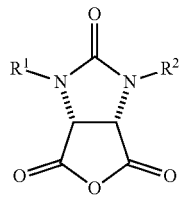
(7)

and an optically active amine compound represented by the following formula (8)

[Formula 8]
Formula 8

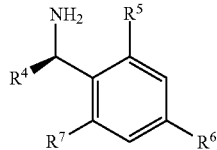
(8)

are reacted in a reaction solvent comprising mesitylene, thereby producing a mixture which comprises an amide compound I represented by the following formula (9)

[Formula 9]
Formula 9

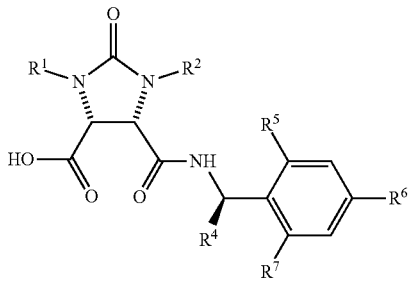
(9)

and an amide compound II represented by the following formula (10)

[Formula 10]
Formula 10

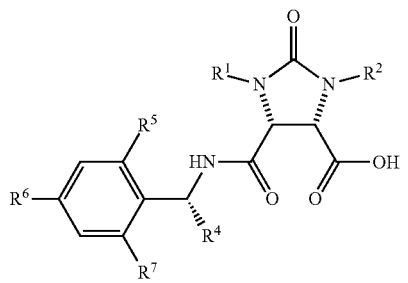
(10)

a first reaction solution comprising the obtained mixture and mesitylene is refluxed to dehydrate the mixture, thereby producing the trione compound represented by the formula (1); and subsequently the obtained trione compound is (ii) reduced by calcium borohydride in ethanol, thereby producing the amide alcohol compound represented by the formula (3).

7. The method according to claim 6, wherein an ureido compound represented by the following formula (11)

[Formula 11]
Formula 11

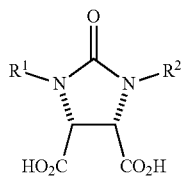
(11)

is dehydrated by refluxing in a reaction solvent comprising mesitylene, thereby producing the anhydride compound represented by the formula (7); and subsequently the obtained anhydride compound is reacted with the optically active amine compound represented by the formula (8).

8. The method according to claim 1, wherein a reaction temperature at the time of reducing by the calcium borohydride in (ii) is −30° C. or more and 50° C. or less.

9. The method according to claim 1, wherein the total number of carbon atoms in a molecule of the alkylene glycol monoalkyl ether is 2 to 6.

10. The method according to claim 1, wherein
a second reaction solution which comprises the anhydride compound represented by the formula (7) and a reaction solvent comprising mesitylene is produced; and
subsequently the second reaction solution and the optically active amine compound represented by the formula (8) are mixed, thereby producing the mixture which comprises the amide compound I represented by the formula (9) and the amide compound II represented by the formula (10).

11. The method according to claim 3, wherein the total number of carbon atoms in a molecule of the alkylene glycol monoalkyl ether is 2 to 6.

12. The method according to claim 6, wherein
a second reaction solution which comprises the anhydride compound represented by the formula (7) and a reaction solvent comprising mesitylene is produced; and subsequently the second reaction solution and the optically active amine compound represented by the formula (8) are mixed, thereby producing the mixture which comprises the amide compound I represented by the formula (9) and the amide compound II represented by the formula (10).

13. A method for producing a lactone compound according to claim 1, further comprising reacting the lactone compound with a thiation agent, thereby producing a thiolactone compound represented by the following formula (5)

[Formula 5]

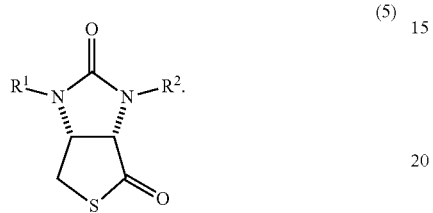

(5)

* * * * *